US009926470B2

(12) United States Patent
Carty

(10) Patent No.: US 9,926,470 B2
(45) Date of Patent: Mar. 27, 2018

(54) HYBRID MATERIAL OF CROSSLINKED MICROGEL PARTICLES DISPERSED IN AN ADHESIVE

(71) Applicant: Avery Dennison Corporation, Glendale, CA (US)

(72) Inventor: Neal Carty, Mentor, OH (US)

(73) Assignee: Avery Dennison Corporation, Glendale, CA (US)

( * ) Notice: Subject to any disclaimer, the term of this patent is extended or adjusted under 35 U.S.C. 154(b) by 0 days.

(21) Appl. No.: 14/437,358

(22) PCT Filed: Oct. 21, 2013

(86) PCT No.: PCT/US2013/065812
§ 371 (c)(1),
(2) Date: Apr. 21, 2015

(87) PCT Pub. No.: WO2014/066195
PCT Pub. Date: May 1, 2014

(65) Prior Publication Data
US 2015/0284597 A1 Oct. 8, 2015

Related U.S. Application Data

(60) Provisional application No. 61/716,828, filed on Oct. 22, 2012.

(51) Int. Cl.
| | | |
|---|---|---|
| *C09J 183/04* | (2006.01) | |
| *C09J 7/02* | (2006.01) | |
| *A61L 15/58* | (2006.01) | |
| *B32B 43/00* | (2006.01) | |
| *C09J 5/00* | (2006.01) | |
| *C08G 77/12* | (2006.01) | |
| *C08G 77/20* | (2006.01) | |
| *C09J 133/00* | (2006.01) | |

(52) U.S. Cl.
CPC ........... *C09J 7/0246* (2013.01); *A61L 15/585* (2013.01); *B32B 43/006* (2013.01); *C09J 5/00* (2013.01); *C09J 7/0285* (2013.01); *C09J 183/04* (2013.01); *C08G 77/12* (2013.01); *C08G 77/20* (2013.01); *C09J 133/00* (2013.01); *C09J 2201/606* (2013.01); *C09J 2205/102* (2013.01); *C09J 2205/11* (2013.01); *C09J 2205/302* (2013.01); *C09J 2433/00* (2013.01); *C09J 2467/005* (2013.01); *C09J 2483/00* (2013.01); *Y10T 156/1111* (2015.01); *Y10T 428/1457* (2015.01); *Y10T 428/259* (2015.01); *Y10T 428/2891* (2015.01)

(58) Field of Classification Search
CPC .................. C09J 11/08; C09J 183/04; C09J 133/00–133/16
See application file for complete search history.

(56) References Cited

U.S. PATENT DOCUMENTS

| | | |
|---|---|---|
| 2,292,995 A | 8/1942 | Greenwoll |
| 2,552,520 A | 5/1951 | Coler |
| 3,085,024 A | 4/1963 | Blackford |
| 3,143,208 A | 8/1964 | Sizemore |
| 3,339,546 A | 9/1967 | Chen |
| 3,457,919 A | 7/1969 | Harbard |
| 3,471,445 A | 10/1969 | Carr |
| 3,485,349 A | 12/1969 | Verne |
| 3,568,829 A | 3/1970 | Brady |
| 3,530,494 A | 9/1970 | Baratta |
| 3,554,835 A | 1/1971 | Burton |
| 3,635,383 A | 1/1972 | Waltz |
| 3,645,198 A | 2/1972 | Field |
| 3,672,550 A | 6/1972 | Greco |
| 3,688,465 A | 9/1972 | Benitez et al. |
| 3,702,584 A | 11/1972 | Field |
| 3,837,338 A | 9/1974 | Chesky et al. |
| 3,885,070 A | 5/1975 | Chapman |

(Continued)

FOREIGN PATENT DOCUMENTS

| | | |
|---|---|---|
| EP | 0254696 | 1/1988 |
| EP | 1184039 | 3/2002 |

(Continued)

OTHER PUBLICATIONS

English translation of JP2002-003817A.*
Silicone Powders Product description from Shin Etsu (no date).*
Chivers, Easy removal of pressure sensitive adhesives for skin applications, International Journal of Adhesion & Adhesives, 2001, 381-388, Elsevier Science, Ltd.
Cutting, Impact of adhesive surgical tape and wound dressings on the skin, with reference to skin stripping, Journal of Wound Care, Apr. 2008, 157-162, vol. 17, No. 4.
Dykes et al., Effects of adhesive dressings on the stratum corneum of the skin, The Journal of Wound Care, Feb. 2001, 7-10, vol. 10, No. 2.
International Preliminary Report on Patentability dated Dec. 19, 2014 issued in corresponding International Application No. PCT/US13/065812.

(Continued)

*Primary Examiner* — Marc S Zimmer
(74) *Attorney, Agent, or Firm* — Mark E. Bandy; Rankin, Hill & Clark LLP

(57) ABSTRACT

A two-phase adhesive composition and selective debonding agent are described. The adhesive composition comprises a substantially continuous first phase comprising a pressure sensitive adhesive and a discontinuous second phase comprising crosslinked silicone gel microparticles. When applied, the selective debonding agent is absorbed by the gel microparticles. The gel microparticles change size or shape and facilitate debonding the adhesive from a substrate by decreasing the contact area between the adhesive and the substrate. Methods to selectively debond pressure sensitive adhesive compositions, methods of making the pressure sensitive adhesive compositions, articles that utilize the pressure sensitive adhesive composition, adhesive systems, and kits that include an article containing the pressure sensitive adhesive composition and the selective debonding agent, are also described.

47 Claims, 9 Drawing Sheets

(56) References Cited

U.S. PATENT DOCUMENTS

| | | |
|---|---|---|
| 3,923,084 A | 12/1975 | Matthews et al. |
| 3,939,108 A | 2/1976 | Sirota et al. |
| 3,998,654 A | 12/1976 | Falaas et al. |
| 4,007,577 A | 2/1977 | Matthews et al. |
| 4,112,213 A | 9/1978 | Waldman |
| 4,151,319 A | 4/1979 | Sackoff et al. |
| 4,156,066 A | 5/1979 | Gould |
| 4,192,785 A | 3/1980 | Chen et al. |
| 4,194,041 A | 3/1980 | Gore et al. |
| 4,231,369 A | 11/1980 | Sorensen et al. |
| 4,317,852 A | 3/1982 | Ogden |
| 4,324,595 A | 4/1982 | Kasprzak |
| 4,336,166 A | 6/1982 | Penczuk et al. |
| 4,346,189 A | 8/1982 | Laurent |
| 4,346,700 A | 8/1982 | Dunshee |
| 4,367,732 A | 1/1983 | Poulsen et al. |
| 4,429,242 A | 1/1984 | Layh |
| 4,464,202 A | 8/1984 | Andres et al. |
| 4,465,729 A | 8/1984 | Cancio |
| 4,472,480 A | 9/1984 | Olson |
| 4,477,325 A | 10/1984 | Osburn |
| 4,493,870 A | 1/1985 | Vrouenraets |
| 4,505,976 A | 3/1985 | Doehnert et al. |
| 4,532,316 A | 7/1985 | Henn |
| 4,551,490 A | 11/1985 | Doyle et al. |
| 4,552,138 A | 11/1985 | Hofeditz et al. |
| 4,562,102 A | 12/1985 | Hanson |
| 4,584,192 A | 4/1986 | Dell et al. |
| 4,584,355 A | 4/1986 | Blizzard et al. |
| 4,585,836 A | 4/1986 | Homan et al. |
| 4,591,622 A | 5/1986 | Blizzard et al. |
| 4,655,767 A | 4/1987 | Woodard et al. |
| 4,680,210 A | 7/1987 | Corcoran |
| 4,693,935 A | 9/1987 | Mazurek |
| 4,725,481 A | 2/1988 | Ostapchenko |
| 4,730,439 A | 3/1988 | Chung et al. |
| 4,738,257 A | 4/1988 | Meyer et al. |
| 4,743,232 A | 5/1988 | Kruger |
| 4,772,499 A | 9/1988 | Greenway |
| 4,780,168 A | 10/1988 | Beisang et al. |
| 4,807,753 A | 2/1989 | Goldstein |
| 4,842,577 A | 6/1989 | Konno et al. |
| 4,867,981 A | 9/1989 | Grof |
| 4,917,112 A | 4/1990 | Kalt |
| 4,945,713 A | 8/1990 | Widenback |
| 4,952,618 A | 8/1990 | Olsen |
| 4,977,892 A | 12/1990 | Ewall |
| 4,987,893 A | 1/1991 | Salamone et al. |
| 5,004,502 A | 4/1991 | Ramzan |
| 5,028,653 A | 7/1991 | Desmonceau |
| 5,032,637 A | 7/1991 | Therriault et al. |
| 5,045,601 A | 9/1991 | Capelli et al. |
| 5,103,812 A | 4/1992 | Salamone et al. |
| 5,154,922 A | 10/1992 | Govil et al. |
| 5,156,911 A | 10/1992 | Stewart |
| 5,183,841 A | 2/1993 | Bernard |
| 5,209,969 A | 5/1993 | Crowther |
| 5,213,565 A | 5/1993 | Rollband |
| 5,270,358 A * | 12/1993 | Asmus ............... A61L 24/043 424/448 |
| 5,308,887 A | 5/1994 | Ko et al. |
| 5,336,207 A | 8/1994 | Norcia |
| 5,369,155 A | 11/1994 | Asmus |
| 5,385,965 A | 1/1995 | Bernard et al. |
| 5,387,450 A | 2/1995 | Stewart |
| 5,405,643 A | 4/1995 | Scholz |
| 5,412,035 A | 5/1995 | Schmitt et al. |
| 5,496,605 A | 3/1996 | Augst |
| 5,507,386 A | 4/1996 | Foote |
| 5,609,932 A | 3/1997 | Goetz et al. |
| 5,626,955 A | 5/1997 | Goetz et al. |
| 5,636,643 A | 6/1997 | Argenta et al. |
| 5,645,081 A | 7/1997 | Argenta et al. |
| 5,725,491 A | 3/1998 | Tipton et al. |
| 5,763,038 A | 6/1998 | Wood |
| 5,803,639 A | 9/1998 | Gusakov et al. |
| 5,827,579 A | 10/1998 | Groshens |
| 5,843,018 A | 12/1998 | Shesol et al. |
| 5,889,118 A | 3/1999 | Delgado et al. |
| 5,907,018 A | 5/1999 | Mazurek |
| 5,931,304 A | 8/1999 | Hammond |
| 5,941,413 A | 8/1999 | Roman |
| 5,971,138 A | 10/1999 | Soughan |
| 5,990,199 A | 11/1999 | Bealing et al. |
| 6,018,092 A | 1/2000 | Dunshee |
| 6,045,895 A | 4/2000 | Hyde et al. |
| 6,048,806 A | 4/2000 | Deeb |
| 6,063,231 A | 5/2000 | Adler et al. |
| 6,090,076 A | 7/2000 | Lane, Jr. |
| 6,107,219 A | 8/2000 | Joseph et al. |
| 6,177,163 B1 | 1/2001 | Blok et al. |
| 6,191,338 B1 | 2/2001 | Haller et al. |
| 6,302,867 B1 | 10/2001 | Brown, Jr. et al. |
| 6,306,497 B1 | 10/2001 | Wang |
| 6,368,687 B1 | 4/2002 | Joseph et al. |
| 6,436,227 B1 | 8/2002 | Adler |
| 6,480,210 B1 | 11/2002 | Martino et al. |
| 6,495,229 B1 | 12/2002 | Carte et al. |
| 6,503,231 B1 | 1/2003 | Prausnitz et al. |
| 6,541,098 B2 | 4/2003 | Venkatasanthanam et al. |
| 6,583,220 B1 | 6/2003 | Lipman |
| 6,607,799 B1 | 8/2003 | Heinecke |
| 6,610,762 B1 | 8/2003 | Webster |
| 6,630,049 B2 | 10/2003 | Hannington et al. |
| 6,630,238 B2 | 10/2003 | Hyde et al. |
| 6,632,522 B1 | 10/2003 | Hyde et al. |
| 6,756,095 B2 | 6/2004 | Sandt et al. |
| 6,756,102 B1 | 6/2004 | Galo |
| 6,794,318 B2 | 9/2004 | Anderson et al. |
| 6,805,184 B1 | 10/2004 | Hsiu-Man |
| 6,927,315 B1 | 8/2005 | Heinechk et al. |
| 6,929,128 B2 | 8/2005 | Caldwell et al. |
| 7,004,354 B2 | 2/2006 | Harper |
| 7,078,582 B2 | 7/2006 | Stebbings et al. |
| D540,535 S | 4/2007 | Dunshee |
| D542,022 S | 5/2007 | Dunshee |
| D542,023 S | 5/2007 | Dunshee |
| D543,349 S | 5/2007 | Dunshee |
| 7,223,468 B2 | 5/2007 | Furumori |
| D544,203 S | 6/2007 | Dunshee |
| 7,259,190 B2 | 8/2007 | Lykke |
| 7,270,861 B2 | 9/2007 | Broering et al. |
| 7,270,862 B2 | 9/2007 | Barriere et al. |
| 7,322,543 B2 | 1/2008 | Moores |
| 7,332,205 B2 | 2/2008 | Hannington et al. |
| 7,344,618 B2 | 3/2008 | Hannington et al. |
| 7,354,889 B2 | 4/2008 | Askill |
| 7,396,976 B2 | 7/2008 | Hurwitz et al. |
| 7,399,800 B2 | 7/2008 | Burch |
| 7,612,248 B2 | 11/2009 | Burton et al. |
| 7,666,448 B2 | 2/2010 | Mower |
| D611,156 S | 3/2010 | Dunshee |
| D611,456 S | 3/2010 | Sung |
| 7,833,577 B2 | 11/2010 | Bries |
| 7,842,752 B2 | 11/2010 | Bougherara |
| 7,901,532 B2 | 3/2011 | Bain et al. |
| 8,528,731 B2 | 9/2013 | Bratter et al. |
| 2001/0043943 A1 | 11/2001 | Coffey |
| 2001/0055618 A1 | 12/2001 | Inokuchi |
| 2002/0034913 A1 | 3/2002 | Curro et al. |
| 2002/0039867 A1 | 4/2002 | Curro et al. |
| 2002/0082539 A1 | 6/2002 | Battah |
| 2002/0151865 A1 | 10/2002 | McLaughlin et al. |
| 2002/0164446 A1 | 11/2002 | Zhou et al. |
| 2003/0039790 A1 | 2/2003 | Janetzke |
| 2003/0152732 A1 | 8/2003 | Donahue |
| 2003/0186016 A1 | 10/2003 | Garvic et al. |
| 2003/0203192 A1 | 10/2003 | Kiuchi |
| 2004/0111072 A1 | 6/2004 | McKissick |
| 2005/0031860 A1 | 2/2005 | Katsushiro |
| 2005/0048244 A1 | 3/2005 | Do et al. |
| 2005/0084640 A1 | 4/2005 | Bilodeau et al. |
| 2005/0089663 A1 | 4/2005 | Wong et al. |
| 2005/0178783 A1 | 8/2005 | Pastan et al. |

(56) References Cited

U.S. PATENT DOCUMENTS

| | | | |
|---|---|---|---|
| 2006/0030808 A1 | 2/2006 | Kennedy | |
| 2006/0162850 A1 | 7/2006 | Lake et al. | |
| 2007/0010777 A1 | 1/2007 | Dunshee | |
| 2007/0054821 A1 | 3/2007 | Askill | |
| 2007/0154670 A1 | 7/2007 | Hannington | |
| 2008/0173404 A1 | 7/2008 | Guillory | |
| 2008/0223397 A1 | 9/2008 | Yates | |
| 2008/0280086 A1 | 11/2008 | Bries | |
| 2009/0229732 A1 | 9/2009 | Averaerts | |
| 2010/0101723 A1 | 4/2010 | Okamoto et al. | |
| 2010/0120646 A1 | 5/2010 | Leroy | |
| 2010/0129583 A1 | 5/2010 | Hong et al. | |
| 2011/0024586 A1 | 2/2011 | Brinkdopke et al. | |
| 2011/0033515 A1 | 2/2011 | Harpstead et al. | |
| 2014/0194838 A1* | 7/2014 | Wibaux | C09J 7/0246 604/319 |
| 2015/0291858 A1* | 10/2015 | Nishimura | C09J 133/08 428/344 |

FOREIGN PATENT DOCUMENTS

| | | |
|---|---|---|
| EP | 2078517 | 7/2009 |
| EP | 2123728 | 11/2009 |
| JP | S10-03864 | 4/1935 |
| JP | S59-100432 | 7/1984 |
| JP | S61-136748 | 8/1986 |
| JP | 10-314214 | 12/1998 |
| JP | 2001-512357 | 8/2001 |
| JP | 2001-524357 | 12/2001 |
| JP | 2002003817 | 1/2002 |
| JP | 2006-025918 | 2/2006 |
| JP | 2009-028137 | 2/2009 |
| JP | 2009-297434 | 12/2009 |
| WO | 90/10028 | 9/1990 |
| WO | 92/20751 | 11/1992 |
| WO | 93/00788 | 1/1993 |
| WO | 93/23446 | 1/1994 |
| WO | 96/25469 | 8/1996 |
| WO | 99/11728 | 3/1999 |
| WO | 99/14282 | 3/1999 |
| WO | 99/27975 | 6/1999 |
| WO | 00/04348 | 1/2000 |
| WO | 01/19306 | 3/2001 |
| WO | 02/083206 | 10/2002 |
| WO | 02/095655 | 11/2002 |
| WO | 2007/140785 | 12/2007 |
| WO | 07/145996 | 2/2008 |
| WO | 09/105297 | 10/2009 |
| WO | 2010/124187 | 10/2010 |
| WO | 2010/129299 | 11/2010 |
| WO | 2011/100181 | 8/2011 |

OTHER PUBLICATIONS

International Search Report and Written Opinion dated Dec. 18, 2013 issued in corresponding International Application No. PCT/US13/065812.
Rippon et al., Skin adhesives and their role in wound dressings, Wounds UK, 2007, vol. 3, No. 4.
Waring et al., Skin adhesion properties of three dressings used for acute wounds, Wounds UK, 2009, 22-31, vol. 5.
Webster, Recent developments in pressure-sensitive adhesives for medical applications, International Journal of Adhesion & Adhesives, 1997, 69-73, Elsevier Science, Ltd.
Webster, The development of a pressure-sensitive adhesive for trauma-free removal, International Journal of Adhesion & Adhesives, 1999, 29-34, Elsevier Science, Ltd.
Invitation to Pay Additional Fees dated Jul. 19, 2012 issued in corresponding International Application No. PCT/US2010/032610 filed Apr. 27, 2010.
International Search Report dated Sep. 5, 2012 issued in corresponding International Application No. PCT/US2010/032610 filed Apr. 27, 2010.
Written Opinion dated Sep. 5, 2012 issued in corresponding International Application No. PCT/US2010/032610 filed Apr. 27, 2010.
International Preliminary Report on Patentability dated Sep. 18, 2012 issued in corresponding International Application No. PCT/US2010/032610 filed Apr. 27, 2010.
J. Moffatt, P.J. Franks, H. Hollingsworth, Position document, European Wound Management Association (EMMA) London, UK Medical Partnerships Ltd. p. 1-17, 2002.
"Skin Irritation Due to Repetitive Application of Adhesive Tape; the Influence of Adhesive Strength and Seasonal Variability," F. Tokumura; K. Umekage; M. Sado; S. Otsuka; S. Suda; M. Taniguchi; A. Yamori; A. Nakamura; J. Kawai; K. Ika, Skin Research and Technology, 11, 102-106 (2005).
"Using Protective Skin Wipes Under Adhesive Tapes," Dealy C., J., Journal of Wound Care Jul./Aug., vol. 1, No. 2, 1992.
International Preliminary Report on Patentability dated Mar. 6, 2014 issued in corresponding International Application No. PCT/US2012/036999 filed May 9, 2012.
International Search Report dated Jul. 30, 2012 issued in corresponding International Application No. PCT/US2012/036999 filed May 9, 2012.
Written Opinion dated Jul. 30, 2012 issued in corresponding International Application No. PCT/US2012/036999 filed May 9, 2012.
International Preliminary Report on Patentability dated Aug. 14, 2012 issued in corresponding International Application No. PCT/US2011/023853 filed Feb. 7, 2011.
International Search Report and Written Opinion dated Oct. 24, 2012 issued in corresponding International Application No. PCT/US2012/047980 filed Jul. 24, 2012.
International Preliminary Report on Patentability dated Apr. 15, 2014 issued in corresponding international Application No. PCT/US2012/047980 filed Jul. 24, 2012.
International Search Report and Written Opinion dated Aug. 13, 2013 issued in corresponding PCT/US2011/055745 filed Oct. 11, 2011.
International Search Report and Written Opinion dated Apr. 20, 2011 issued in corresponding International Application No. PCT/US2011/023853 filed Feb. 7, 2011.
International Search Report and Written Opinion dated Apr. 5, 2013 issued in corresponding International Application No. PCT/US2012/065196 filed Nov. 15, 2012.
International Preliminary Report on Patentability dated Jan. 25, 2015 issued in corresponding International Application No. PCT/US2012/065196 filed Nov. 15, 2012.
"Dynarex Antiseptic/Infection Control Products", Dynarex, URL: http://www.dynarex.com/productdetails.asp?subcat=5, Feb. 14, 2012.

* cited by examiner

1% SILICONE

500 μm

10% SILICONE

500 μm

HYBRID MATERIAL OF CROSSLINKED MICROGEL PARTICLES DISPERSED IN AN ADHESIVE

CROSS-REFERENCE TO RELATED APPLICATION

The present application is a 371 of International Application No. PCT/US2013/065812, which was published in English on May 1, 2014, and claims the benefit of U.S. Provisional Patent Application No. 61/716,828 filed Oct. 22, 2012, both of which are incorporated herein by reference in their entireties.

FIELD

The present subject matter relates to a two-phase adhesive composition including microparticles, a selective debonding agent for debonding the adhesive, a method of using the adhesive, a method of debonding the adhesive with the selective debonding agent, methods of making the adhesive, articles that utilize the adhesive, systems of adhesive and debonding agents, and a kit that includes an adhesive article and a selective debonding agent.

BACKGROUND

Adhesives are widely used for securing a variety of articles to substrates. Pressure sensitive adhesives (PSA) are well known and are used for a variety of industrial, consumer, and medical applications. Pressure sensitive adhesives are characterized as being normally tacky and exhibiting instant tack when applied to a substrate. A variety of polymers have been used to manufacture pressure sensitive adhesives, for example, acrylic and methacrylic ester homo- or copolymers, butyl rubber-based systems, silicones, nitriles, styrene block copolymers, ethylene-vinyl acetate, urethanes, vinyl esters and amides, olefin copolymer materials, natural or synthetic rubbers, and the like.

Pressure sensitive adhesives have been widely studied in an attempt to tailor their properties so that they readily debond from a given substrate. It is especially desirable for skin-contact adhesives, such as those used in wound dressings, to have very high initial adhesion. This enables them to be easily applied, remain securely attached in place, and act as good barriers against external microbial contaminants. At the same time, it is preferred that the adhesive be easy to remove. Tissue trauma resulting from removal of adhesive articles is a well-documented phenomenon that can delay wound healing, increase wound size, and cause significant pain.

There are numerous strategies for mitigating the trauma associated with removing skin adhesives. Some strategies employ a debonding agent to the article that reacts with the adhesive causing a loss of adhesion. Other strategies deactivate the adhesive on demand by using an external trigger, such as temperature changes, light exposure, hydration, or the like. Other strategies simply rely on striking a compromise between adhesive strength and ease of removal, soft silicone adhesives being an excellent example. These efforts have often led to less than optimum results. The problems include unsatisfactory reduction in bonding strength or the dissolution of the pressure sensitive adhesive in the debonding agent. When the pressure sensitive adhesive dissolves, it can leave a tacky residue on the substrate subsequent to removal.

While prior efforts have been undertaken to incorporate microparticles or microcapsules in a pressure sensitive adhesive, such efforts have had limitations and problems. Various types of microparticles and microcapsules have included blowing agents, water soluble tackifiers, or hydrocolloid particles. These strategies have led to two problems: 1) a significant decrease in the initial bonding strength of the adhesive; and 2) a need to use an undesirable debonding agent such as heat, ultraviolet light, or acidic or basic solutions.

Pressure sensitive adhesives have been incorporated into a wide variety of products including those used in medical applications, automobile applications, and adhesive tapes. While many commercial products are known to facilitate removing an adhesive article from a substrate, there remains a need to utilize a selective debonding agent to facilitate the removal of such articles.

SUMMARY

The difficulties and drawbacks associated with previously known adhesives and strategies are overcome in the present compositions, adhesives, articles using such, and related methods.

The present subject matter relates to crosslinked silicone gel microparticles (also referred to herein as "microgel particles", "microgels", and/or "microparticles") that expand upon exposure to a debonding fluid to assist in adhesive removal.

In one aspect, the present subject matter provides a pressure sensitive adhesive composition adapted for selective debonding comprising a pressure sensitive adhesive and crosslinked silicone gel microparticles dispersed therein. The microparticles are such that they undergo a change in at least one of shape and volume when exposed to a selective debonding agent.

In another aspect, the present subject matter provides a selectively debondable adhesive system. The system comprises a selective debonding agent and a pressure sensitive adhesive composition. The pressure sensitive adhesive composition includes a pressure sensitive adhesive and crosslinked silicone gel microparticles dispersed therein. The microparticles are such that they undergo a change in at least one of shape and volume when exposed to the selective debonding agent.

In another aspect, the present subject matter provides a method of preparing a pressure sensitive adhesive composition adapted for selective debonding comprising a pressure sensitive adhesive and crosslinked silicone gel microparticles dispersed therein. The microparticles are such that they undergo a change in at least one of shape and volume when exposed to a selective debonding agent.

In another aspect, the present subject matter provides a method of debonding an article containing a pressure sensitive adhesive composition adapted for selective debonding. The method comprises providing an article which is adhesively bonded to a substrate, selecting a debonding agent, applying the debonding agent to the pressure sensitive adhesive, and peeling the article from the substrate. The pressure sensitive adhesive composition comprises a pressure sensitive adhesive and crosslinked silicone gel microparticles dispersed therein. The microparticles are such that they undergo a change in at least one of shape and volume when exposed to a selective debonding agent. The method includes selecting a debonding agent that will be absorbed by the crosslinked silicone gel microparticles and change their shape and/or volume, thus reducing the adhesion between the pressure sensitive adhesive and the substrate. The debonding agent is such that it will not be absorbed by, or dissolve the pressure sensitive adhesive.

In another aspect, the present subject matter provides an article comprising a backing material having first and second oppositely directed surfaces, a pressure sensitive adhesive composition disposed on the first surface of the backing material, and a product release liner adhered to the exposed surface of the pressure sensitive adhesive composition. The pressure sensitive adhesive composition is adapted for selective debonding and comprises a pressure sensitive adhesive and crosslinked silicone gel microparticles dispersed therein. The microparticles are such that they undergo a change in at least one of shape and volume when exposed to a selective debonding agent.

In another aspect, the present subject matter provides a kit comprising a backing material, a pressure sensitive adhesive composition disposed on the backing material for applying the backing material to a substrate, and a selective debonding agent for removing the backing material from a substrate. The pressure sensitive adhesive composition is adapted for selective debonding and includes a pressure sensitive adhesive matrix, crosslinked silicone gel microparticles dispersed in the pressure sensitive adhesive matrix with a characteristic such that upon exposure to a debonding agent, the microparticles undergo a change in at least one of shape and volume.

As will be realized, the subject matter described herein is capable of other and different embodiments and its several details are capable of modifications in various respects, all without departing from the claimed subject matter. Accordingly, the drawings and description are to be regarded as illustrative and not restrictive.

BRIEF DESCRIPTION OF THE DRAWINGS

These, as well as other features, aspects, and advantages of this present subject matter, will be more completely understood and appreciated by referring to the following more detailed description of the exemplary embodiments of the present subject matter in conjunction with the accompanying drawings.

DETAILED DESCRIPTION OF THE EMBODIMENTS

Figure 1:
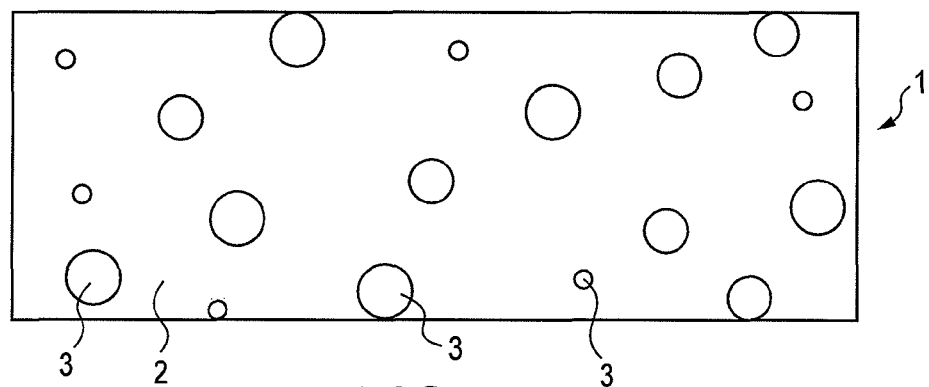
FIG. 1 is a schematic, cross sectional view of a preferred embodiment adhesive in accordance with the present subject matter.

The subject matter described herein provides compositions for adhesively bonding an article to a substrate and easily and selectively removing the article from the substrate. The adhesive compositions comprise particular microparticles dispersed within an adhesive matrix. The microparticles of the present subject matter change shape and/or increase in size when exposed to a selective debonding agent. A change in shape and/or size is generally referred to herein as "swelling." Exposure to aqueous solutions, such as water or exudate from a wound, typically will not cause size or shape changes in the microparticles. The selective debonding agent typically does not dissolve the adhesive matrix.

A related method of using and debonding the adhesive article from a substrate is described. The method to debond the article from a substrate is inexpensive, practical, and can be readily controlled by the user. The method does not require the use of heat, light, or a change in pH to facilitate debonding. An adhesive article comprising the adhesive composition of the present subject matter is provided and applied to a substrate. When removal of the article is desired, a selective debonding agent is applied to the adhesive composition at the interface between the substrate and the article. The microparticles at the interface that are exposed to the debonding agent will absorb at least a portion of the debonding agent and expand and/or change shape. As the microparticles swell at the interface, they push or otherwise displace the adhesive matrix away from the substrate causing the adhesive matrix to partially debond from the substrate. This produces a reduction in the surface contact area between the substrate and the adhesive matrix. As less of the surface of the adhesive matrix is contacting the substrate, less force is required for removal of the adhesive article. This allows for easy removal.

A related method of preparing the adhesive composition of the present subject matter has another advantage in its simple and inexpensive means of production. The preparation is accomplished by mixing a two-part silicone gel component system in a solution of water and surfactant. The two-part silicone gel components are combined just prior to mixing them in the water and surfactant solution. Once the gel components are mixed with the solution, the mixture is agitated and heated to uniformly disperse droplets of uncured silicone gel in the water solution. The silicone gel droplets cure and at least partially crosslink to form silicone gel microparticles in suspension in the aqueous solution. The suspension is optionally cooled. The microparticles are then extracted using a solvent. The solvent containing silicone gel microparticles is then combined with a pressure sensitive adhesive. At least a portion of the excess solvent is evaporated to produce a pressure sensitive adhesive with cured and crosslinked silicone gel microparticles dispersed therein.

A preferred embodiment of the present subject matter is a pressure sensitive adhesive composition adapted for selective debonding. The composition comprises a solvent acrylic pressure sensitive adhesive and crosslinked silicone gel microparticles dispersed in the pressure sensitive adhesive. The silicone gel, in the form of microparticles, has characteristics such that upon exposure to a selective debonding agent, the microparticles undergo a change in shape and/or increase in volume. These and other aspects are described in greater detail herein as follows.

Microparticles

In one aspect, the present subject matter relates to microparticles that are contained within the pressure sensitive adhesive matrix. The microparticles provide for the debonding of an adhesive article from a substrate. Several characteristics of the microparticles can be tailored to optimize debonding. Depending on the intended application, one or all of these characteristics can be adjusted to accommodate the particular needs of the user. Some of these characteristics are dependent on or at least influenced by other characteristics of the microparticles, by traits of the pressure sensitive adhesive, and by qualities of the debonding agent. These relationships and related characteristics are as follows.

1. Dispersion within a Pressure Sensitive Adhesive

Microparticle dispersion within a pressure sensitive adhesive matrix is one factor that could affect the debonding mechanism of the present subject matter. Microparticles can be dispersed either uniformly throughout or localized to one region of the pressure sensitive adhesive matrix. The chosen configuration of microparticles within the pressure sensitive adhesive composition will depend on a number of factors including but not limited to: cost, time, intended purpose, method of combining the microparticles to the pressure sensitive adhesive, method of applying the pressure sensitive adhesive composition to an adhesive article, and the like.

Limiting or not limiting microparticle dispersion to certain regions within the pressure sensitive adhesive matrix for example could depend on intended application.

Localizing microparticles at or near a surface of a pressure sensitive adhesive layer may become preferred in certain applications where a backing layer of an adhesive article is present. Generally dispersing microparticles within the pressure sensitive adhesive composition may lead to debonding of the backing material from the pressure sensitive adhesive composition. If microparticles that are adjacent to a backing layer become exposed to a debonding agent, swelling of the microparticles may cause the backing layer to debond from the pressure sensitive adhesive composition rather than having the adhesive article and pressure sensitive adhesive composition debond collectively from the substrate. This would undesirably leave the pressure sensitive adhesive composition adhered to the substrate. Restricting the microparticles to the substrate side of the pressure sensitive adhesive composition would limit this result.

Alternatively, in other applications, it may become desirable to generally disperse the microparticles within the pressure sensitive adhesive. This could be desirable where a pressure sensitive adhesive composition is intended to be left on the substrate with no backing layer. The pressure sensitive adhesive could then be applied via a carrier layer, by spraying means, by brushing means, or the like.

Microparticles, in accordance with the present subject matter, are preferably dispersed uniformly within the pressure sensitive adhesive composition. In another preferred embodiment, the microparticles are concentrated near one or more regions of the pressure sensitive adhesive matrix layer.

Figure 2:
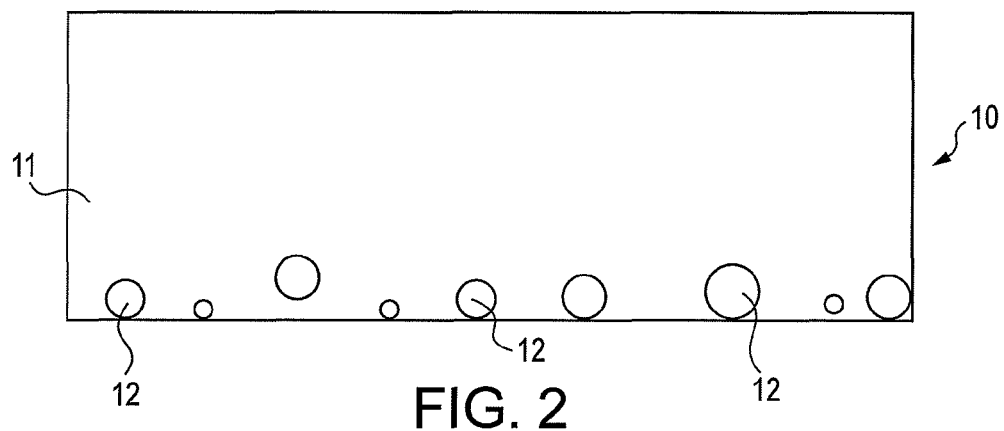
FIG. 2 is a schematic, cross sectional view of another preferred embodiment adhesive in accordance with the present subject matter.

Referring to the figures wherein the drawings are for purposes of illustrating the preferred embodiments of the present subject matter only and not for purposes of limiting same, and initially to FIG. 1 and FIG. 2, there is shown a pressure sensitive adhesive matrix 1, 10 respectively, comprising a pressure sensitive adhesive 2, 11 respectively, and microparticles 3, 12 respectively, dispersed therein and in accordance with preferred embodiments of the present subject matter.

In accordance with one preferred embodiment and as shown in FIG. 1, the microparticles 3 are dispersed generally uniformly within the pressure sensitive adhesive 2. In accordance with another preferred embodiment and as shown in FIG. 2, the microparticles 12 can be dispersed generally along one surface or region of the pressure sensitive adhesive 11.

With both embodiments respectively, the microparticles 3, 12 constitute a distinct phase from the pressure sensitive adhesives 2, 11 and are not dissolved in the pressure sensitive adhesives. The microparticles have their own discrete shape, independent from the overall contour of the pressure sensitive adhesive layer.

Localized microparticle dispersion within the pressure sensitive adhesive matrix as generally shown in FIG. 2 can be related to the ratio of microparticle size to pressure sensitive adhesive layer thickness. Pressure sensitive adhesives are usually layered in adhesive articles at thicknesses between 30 and 100 micrometers. If the size of the microparticles approaches the thickness of the pressure sensitive adhesive layer, then the microparticles could not be dispersed generally along an outer surface or region of the pressure sensitive adhesive matrix and thereby define one or more other regions within the pressure sensitive adhesive which are free or substantially free of the microparticles. The relatively large microparticles would then extend completely through the pressure sensitive adhesive layer from one surface or region to another. To achieve microparticle dispersion on a surface of the pressure sensitive adhesive, microparticle size should be tailored in relation to the thickness of the pressure sensitive adhesive layer. A pressure sensitive adhesive matrix as shown in FIG. 2 could then be prepared.

Microparticle dispersion is also related to the amount of particles added to the pressure sensitive adhesive matrix. Increasing the amount of microparticles could prevent localized dispersion of the microparticles to certain regions of the pressure sensitive adhesive composition.

The methods used to combine the microparticles to the pressure sensitive adhesive will also influence the dispersion arrangement. Techniques of combining the microparticles and the pressure sensitive adhesive can be customized in order to prepare the dispersion arrangements as depicted in FIG. 1 and FIG. 2. These techniques will be discussed further under the Methods of Preparation section herein.

2. Material Composition

Choice of materials used to prepare the microparticles in accordance with the present subject matter is dependent on a number of considerations. In accordance with the present subject matter, the composition of the microparticles is preferably chosen in relation to the debonding agent employed, the type of pressure sensitive adhesive in which the microparticles will be incorporated, and the intended use of the composition.

The microparticles preferably respond to a specific debonding agent, causing them to swell. When included in a pressure sensitive adhesive composition that is part of an adhesive article, the change in the microparticles aids in the debonding process.

The microparticles preferably do not dissolve in or chemically react with the pressure sensitive adhesive. This will prevent the microparticles from dissolving or swelling when incorporated into the pressure sensitive adhesive and at a time before the adhesive is applied to a substrate. Cross-reactivity between the pressure sensitive adhesive and the microparticles could cause a number of problems. The pressure sensitive adhesive could lose an amount of tackiness due to the dissolving microparticles, inhibiting full adhesion. The pressure sensitive adhesive could otherwise be dissolved by the microparticles, leaving a sticky film on a substrate upon removal of the adhesive article. If the microparticles expanded from reacting with the pressure sensitive adhesive, they could create a non-smooth adhesive surface on the adhesive article. This could reduce bonding between the adhesive article and a substrate.

The microparticles preferably conform to intended use requirements for the end product. For example, if wound dressings are the intended use, microparticles that do not absorb sweat or exudate are preferred for the pressure sensitive adhesive composition. Silicone gel microparticles would be suitable for such application. The silicone gel microparticles preferably do not absorb exudate from a wound, sweat from a user's skin, or water from the environment such as from bathing or meteorological precipitation. Silicone gel microparticles are also advantageous in that they also exhibit initial tackiness separate and apart from the pressure sensitive adhesive matrix. Upon exposure to a selective debonding agent, the silicone gel microparticles preferably change shape and/or increase in volume. The silicone gel microparticles also lose tackiness after exposure to the debonding agent. Their increase in volume and loss of tackiness both assist in debonding the adhesive article from a substrate.

In a preferred embodiment in accordance with the present subject matter, the microparticles are of certain material composition such that they react with the debonding agent causing the microparticles to change shape and/or increase in volume.

In another preferred embodiment in accordance with the present subject matter, the microparticles of the pressure sensitive adhesive matrix are of a certain material composition such that they do not react with or dissolve in the pressure sensitive adhesive.

In another preferred embodiment in accordance with the present subject matter, the microparticles of the pressure sensitive adhesive matrix are of a certain material composition that they do not react with or dissolve in aqueous solutions.

In another preferred embodiment, the microparticles of the present subject matter preferably include a silicone gel. A two-part (part A and part B) silicone gel component system is used to prepare the microparticles. The multi-component system is comprised of a reactive silicone polymer (A) and crosslinking agent (B). Typically, parts A and B include a vinyl-substituted polydimethylsiloxane base.

Preferably, both parts A and B have the same vinyl-substituted polydimethylsiloxane base. The reactive silicone polymer (A) contains hydrogen atoms bonded directly to the silicon atom.

The crosslinking agent (B) contains at least one vinyl-substituted polydimethylsiloxane as well as a catalyst. The catalyst contains a platinum or rhodium metal complex, and more preferably organometallic compounds. Organometallic compounds are characterized by a metal-carbon bond that is generally of character intermediate between ionic and covalent.

Both parts A and B are easily mixed, and when handled separately, do not cure.

The end product is prepared by a temperature-activated addition polymerization reaction. The tacky silicone gel is produced by thoroughly mixing parts A and B in a ratio of about 1:1, thereby enabling the vinyl-group on the vinyl-substituted silicone to be activated by the catalyst and the hydride containing silicone. This results in crosslinking the silicone so that it will begin to cure. The resultant silicone gel is comprised of elastomeric crosslinked silicone polymers. The time required for the desired curing depends on various factors, such as, for example, the reaction temperature or the catalyst concentration. The polymerization reaction may be inhibited by the presence of amines, sulfur, nitrogen oxide, organotin compounds, and carbon monoxide.

The properties of the fully cured silicone can be influenced in various different ways. For example, the properties can be influenced through varying the ratio of the component parts A and B, by modifying the stoichiometric ratios of the groups responsible for the crosslinking such as the vinyl groups and silicon-hydrogen groups, through the molecular weights of the polysiloxanes used or through the concentration of the filling agent(s) used. In this way silicon gels can be made available that are soft, very adhesive and not friable and exhibit significant adhesion to the skin.

The silicone gel product is preferably a soft, clear, tacky silicone gel that is at least partially crosslinked with medium crosslink density.

The silicone gel microparticles preferably swell to from about 3 to about 20 times their original size upon exposure to volatile small molecule silicone fluids such as hexamethyldisiloxane (HDMS) and do not swell upon exposure to aqueous fluids.

The silicone gel microparticles preferably do not react with the pressure sensitive adhesive. The silicone gel microparticles do not swell or change shape as a result of being exposed to the pressure sensitive adhesive.

The silicone gel microparticles preferably do not react with aqueous solutions. The silicone gel microparticles do not swell or change shape as a result of being exposed to aqueous solutions.

NuSil Technology LLC (Carpenteria, Calif.) provides one such silicone gel component system that is provided in a two part formula: MED-6345 Part A (reactive silicone polymer) and Part B (crosslinking agent).

MED-6345 Part A is a clear, stable liquid that is substantially odorless and is insoluble in water. It has molecular weights of Mn (number average)=62,900; Mw (weight average)=98,200; and Mz (z average)=145,000. It has a flash point of greater than 135° C., contains polydimethylsiloxane, and has a specific gravity of about 0.97. MED-6345 Part B is a clear, stable liquid that can have a slight odor. It has molecular weights of Mn (number average)=35,100; Mw (weight average)=52,000; and Mz (z average)=69,200. It has a vapor pressure of less than about 5 mm Hg and is less than 0.1% soluble in water. MED-6345 Part B contains 10% dimethyl, methylhydrogen siloxane copolymer and has a flash point higher than about 60° C. It has a specific gravity of about 0.94.

Both silicone gel components have an uncured viscosity of about 12,750 cP or 12,750 milliPascal·seconds (mPa·s) at 25° C. The cure may be inhibited by traces of amines, sulfur, nitrogen oxide, organotin compounds, and carbon monoxide. The silicone gel components cure in three hours at 60° C. to form a silicone gel that exhibits 5 mm penetration after 15 seconds on a GCA Precision Penetrometer with a 19.5 g shaft and 6.35 mm diameter foot.

Silicone gels with other characteristics could also be used. A firmer or softer gel could be incorporated which would affect the resulting pressure sensitive adhesive composition. Adding more initial tack, creating a larger particle swell, and decreasing cost are all considerations that could determine component material.

Alternatively, and depending on the application and intended debonding agent, the microparticles also preferably comprise hydrogels, heat-responsive gels, or pH-responsive gels in accordance with the present subject matter.

3. Crosslinking

Crosslinking refers to the linking of one polymer chain to another. When polymer chains are linked together by crosslinking, they lose some of their ability to move as individual polymer chains.

The extent of crosslinking ("crosslink density" or "percent cosslinked") affects the properties of the resulting gel. Low crosslink densities decrease the viscosity of the resulting gel. Intermediate densities produce materials with elastomeric properties. High crosslink densities can result in firm products.

When applied to silicone polymers, this crosslinking process "cures" the two liquid silicone components to form a silicone gel. This requires the presence of a crosslinker. An example of a typical crosslinker is a silicone molecule with multiple functional sites that can react or link with another silicone polymer. Under appropriate conditions (heat, humidity, or ultraviolet light) and in the presence of the crosslinker and a catalyst, the individual polymer chains will link together to form a more complex material. Depending on the base polymer, the crosslink density, and the presence of any reinforcing fillers, this material can range from a rigid film to a flexible rubber or a spongy gel.

Depending on the application, one can adjust the characteristics of the silicon gel microparticles by controlling the crosslink density. Controlling the amount of crosslink density can be done by varying the ratio of the silicone crosslinker component to the reactive silicone polymer. Increasing the ratio of the reactive silicone polymer to the silicone crosslinker will result in a softer gel. Conversely, increasing the ratio of silicone crosslinker to the reactive silicone polymer will result in a firmer gel.

Increased crosslink density will result in less swelling of the microgel particles upon exposure to the selective debonding agent. Increased crosslink density will also result in a harder gel that has reduced tackiness and dissolves less in the presence of the selective debonding agent.

Decreased crosslink density will result in more swelling of the microgel particles upon exposure to the selective debonding agent. Decreased crosslink density will also result in a softer gel that has increased tackiness and dissolves more in the presence of the selective debonding agent.

In a preferred embodiment in accordance with the present subject matter, an intermediate crosslink density is utilized. This is achieved by using a ratio of about 1:1 of reactive silicone polymer to silicone crosslinker by weight, respectively. This results in clear, tacky, silicone gel microparticles in accordance with the present subject matter.

In another embodiment, a high crosslink density is preferable. This is achieved by increasing the ratio of silicone crosslinker to reactive silicone polymer by weight. This results in clear silicone gel microparticles in accordance with the present subject matter. As compared to the intermediate crosslink density microgel particles, these microparticles will be less tacky and firmer; they will both dissolve and swell less in the presence of the debonding agent.

In yet another embodiment, a low crosslink density is preferable. This is achieved by increasing the ratio of reactive silicone polymer to silicone crosslinker by weight. This results in clear silicone gel microparticles in accordance with the present subject matter. As compared to the intermediate crosslink density microgel particles, these microparticles will be more tacky and softer; they will both dissolve and swell more in the presence of the debonding agent.

In all embodiments the silicone gel microparticles are at least partially crosslinked, meaning that at least some of the silicone polymer molecules are joined together with crosslinks.

In certain embodiments, the silicone gel microparticles are described in terms of the extent of their crosslinking. The extent of crosslinking can be expressed on a percentage basis such as 1%, 10%, and so on. Various references are noted herein regarding crosslinking percentage. These references refer to the extent to which a crosslinkable material such as a polymeric material is crosslinked. The percentages are expressed on a scale of 0% to 100% in which 0% represents the state of the material having the minimum extent of crosslinks, and 100% represents the state of the material having the maximum extent of crosslinks.

4. Shape

Microparticles can be of differing shapes, including: crescent-shaped, L-shaped, star-shaped, spherical, cubic, cylindrical, cup-shaped, and the like. These shapes largely depend on the process of manufacture and involve consideration of cost, time, means, and material components. Non-spherical microparticles are often more difficult and expensive to manufacture. Spherical microparticles on the other hand, and silicone microgel particles in particular, can be easily and inexpensively manufactured. They are effective when applied in the present subject matter.

In preferred embodiments as depicted in FIG. 1 and FIG. 2, the microparticles 3, 12 respectively of the present subject matter are generally spherical in shape.

Figure 3:
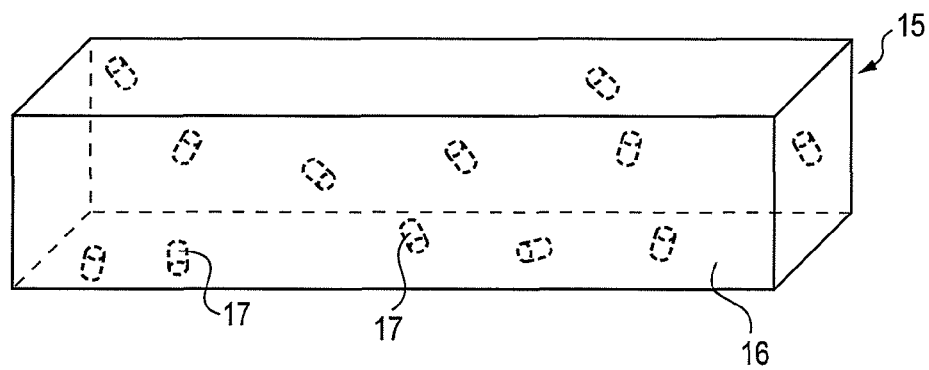
FIG. 3 is a schematic perspective view of another preferred embodiment adhesive in accordance with the present subject matter.

In another aspect, the microparticles can be of any arbitrary shape. FIG. 3 depicts a pressure sensitive adhesive composition 15 comprising a pressure sensitive adhesive 16 and cylindrical-shaped microparticles 17 dispersed therein.

5. Initial Size

Pressure sensitive adhesives are usually layered in adhesive articles at thicknesses from about 30 to about 100 micrometers. When applied to adhesive articles, the exposed face of the pressure sensitive adhesive is releasably attached to a substrate. To be effective in securing the adhesive article to a substrate, the exposed face of the pressure sensitive adhesive generally comprises a smooth surface. This generally smooth surface of the pressure sensitive adhesive promotes a relatively large surface area between the adhesive article and the substrate. The more surface area present between the adhesive article and the substrate, the more adhesion is exhibited between the pressure sensitive adhesive and the substrate.

Because of this phenomenon, it is preferable to have microparticles that are smaller in size at their widest cross section than the thickness of the pressure sensitive adhesive layer in which they are contained. When the size of the particles is thus maintained, they are completely surrounded by the pressure sensitive adhesive and the smooth exposed surface of the pressure sensitive adhesive layer is preserved. The smooth surface allows for proper initial adhesion of the pressure sensitive adhesive to the substrate.

If relatively large microparticles were used, they could potentially stack upon one another and protrude from the pressure sensitive adhesive layer. If they were larger still, single microparticles could, on their own, protrude from the pressure sensitive adhesive layer and compromise the generally smooth surface ideally suited to adhere the adhesive article to a substrate.

To maintain these benefits, and in one embodiment in accordance with the present subject matter, the original size of the microparticles is preferably between 1 and 50 micrometers at the largest cross section and more preferably between 5 and 10 micrometers at their largest cross section.

In accordance with the present subject matter, in applications where the pressure sensitive adhesive is applied in layers thicker than 30 to 100 micrometers, it is possible to utilize microparticles larger than 50 micrometers at their largest cross section.

It is also contemplated to utilize combinations of differently sized microparticles. For example, a first population of relatively large microparticles can be used in combination with a second population of smaller microparticles, all of which are dispersed in a pressure sensitive adhesive, such as shown in FIGS. 1 and 2. The use of additional populations of differently sized microparticles is also contemplated.

6. Expanded Size

After initial application to a substrate, it may be desirable to remove an adhesive article that utilizes the pressure sensitive adhesive matrix containing the microparticles. Removal of the article is aided when the microparticles either change shape, increase their size, or a combination of these changes. The microparticles change shape or increase in volume when they are exposed to and/or respond to a selective debonding agent.

The change in size is affected by the debonding agent chosen and how well the debonding agent is absorbed or reacts with the microparticles. A more complete reaction or absorption will increase the swell size of the microparticles. As discussed herein, the extent of crosslinking will also affect the expanded size of the microparticles.

To debond the adhesive article, one simply has to expose the microparticles to a selective debonding agent at the interface between the article and substrate. The debonding agent can be delivered by using a dropper or other liquid dispenser at the interface, relying on capillary action, spraying, painting, foaming, rubbing, soaking, submerging, brushing, pouring, vapor depositing, syringing, dabbing, squirting, immersing, and misting, or the like.

When the microparticles at the interface are exposed to a debonding agent, they change shape, become larger, or both. They protrude from the smooth adhesive layer creating an uneven surface. These altered microparticles decrease the contact area at the interface between the pressure sensitive adhesive and the substrate. This decrease in surface area reduces the adhesion of the pressure sensitive adhesive and reduces the peel force required to remove the adhesive article from the substrate.

In one preferred embodiment in accordance with the present subject matter, upon exposure to a selective debonding agent, the microparticles at the interface increase in volume. Generally, when exposed to a selective debonding agent, the microparticles will uniformly expand their spherical shape. This will result in microparticles of larger spherical size at the interface. The expanded spheres at the interface decrease the contact surface area between the pressure sensitive adhesive composition and the substrate, causing a decrease in adhesion.

In another preferred embodiment in accordance with the present subject matter, upon exposure to a selective debonding agent, the microparticles change shape. The microparticles can divert from their normal spherical size expansion when a portion of the microparticle extends out of the pressure sensitive adhesive that partially surrounds the microparticles. The portion that extends out of the pressure sensitive adhesive may "balloon" while the portion of the microparticle still contained in the pressure sensitive adhesive may not balloon as much or at all. The term "balloon" as used herein refers to an expansion of the microparticle and typically in an irregular manner so as to form at least one distended or bulging region. This can create a mushroom-shaped microparticle or particles of other varying shapes that decrease the surface area at the interface between the pressure sensitive adhesive composition and the substrate, causing a decrease in adhesion.

In yet another preferred embodiment in accordance with the present subject matter, upon exposure to a selective debonding agent, the microparticles at the interface increase in volume. When exposed to a selective debonding agent, the microparticles will generally uniformly expand their arbitrary shape, which includes spherical, crescent-shape, L-shape, star-shape, cubic, cylindrical, cup-shape, and the like. This will result in microparticles of larger size. The expanded shaped particles at the interface decrease the contact surface area between the pressure sensitive adhesive composition and the substrate, causing a decrease in adhesion.

In accordance with the present subject matter, the preferable expanded size of the microparticles at their largest cross section is between about 3 and about 20 times their original size and more preferably 20 or more times their original size.

In another embodiment in accordance with the present subject matter, the microparticles both change shape and increase in diameter at their largest cross section.

Figure 6A:
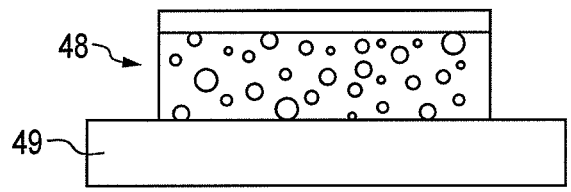
FIGS. 6A-6C are schematic, cross sectional view diagrams of an exemplary system in accordance with the present subject matter for debonding an article from a substrate.
Figure 6B:
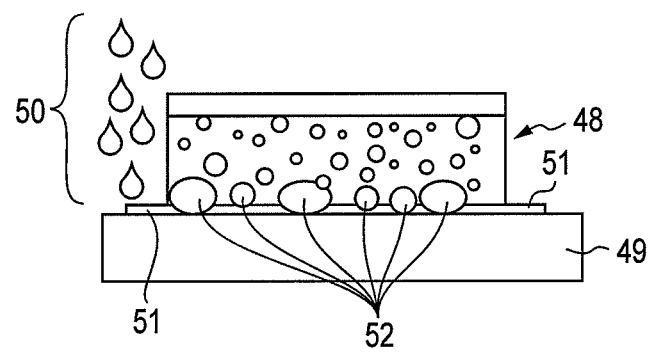
Figure 6C:
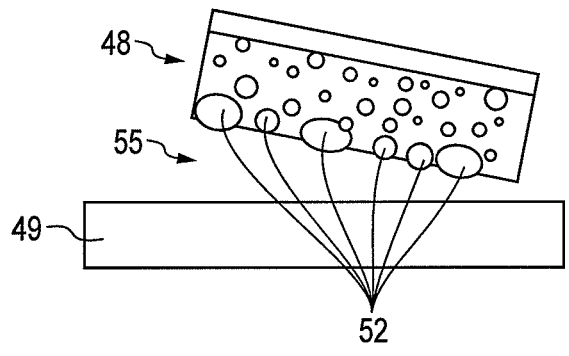

Expanded microparticles are depicted in FIGS. 6A-6C. FIGS. 6A-6C depict sectional view diagrams of an exemplary system in accordance with the present subject matter for debonding an article from a substrate. FIG. 6A shows an adhesive article 48 in accordance with the present subject matter, bonded to a substrate 49. FIG. 6B depicts a selective debonding agent 50 being applied to the substrate-side of the adhesive article 48. An optional fluid conduit layer or member 51 may be utilized along at least a portion of the interface between the adhesive article 48 and the substrate 49. The fluid conduit layer 51 promotes distribution of the debonding agent 50 along the interface. The fluid conduit layer can be formed of porous materials having interior voids, channels or the like. The debonding agent 50 is exposed to or otherwise contacted with microparticles 52 within the pressure sensitive adhesive matrix, and causes the microparticles 52 to expand. The expanded microparticles 52 partially debond, as shown by arrow 55, the adhesive article 48 from the substrate 49 as depicted in FIG. 6C.

7. Tackiness

The crosslinked silicone gel microparticles of the present subject matter, preferably exhibit their own discrete or inherent tackiness. As discussed herein, their degree of tackiness can be influenced by the extent of crosslinking and the composition of silicone gel used to prepare the microparticles. Less crosslink density generally leads to more tackiness, while greater crosslink density generally leads to less tackiness.

If the microparticles did not exhibit their own tackiness, then their inclusion could significantly reduce the overall tackiness of the pressure sensitive adhesive composition. The tackiness of the pressure sensitive adhesive composition though is not compromised as much by the crosslinked silicone gel microparticles. When compared to non-tacky microparticles, silicone gel microparticles do not detract as much from the tackiness of the pressure sensitive adhesive composition as a whole.

Another feature of the preferred silicone gel is that when exposed to a small molecule volatile silicone liquid, the silicone gel loses its tackiness. This mechanism, combined with the swelling effect of the silicone microgel particles, contributes to the debonding effect of the microparticles within the pressure sensitive adhesive composition.

In a preferred embodiment in accordance with the present subject matter, the silicone microgel particles have their own tackiness separate and apart from the pressure sensitive adhesive within which they are contained. Upon exposure to the debonding agent, the microparticles lose their adhesive properties.

8. Proportion to Pressure Sensitive Adhesive Matrix

The proportion of the crosslinked silicone gel microparticles dispersed in the pressure sensitive adhesive matrix can change the initial overall tackiness of the pressure sensitive adhesive composition. The proportion of microparticles can also change the peel force required for removal of an adhesive article from a substrate. These are competing interests involved in choosing the amount of microparticles to incorporate into the pressure sensitive adhesive composition.

If the pressure sensitive adhesive is more tacky than the silicone gel microparticles, which will likely be the situation, then incorporating microparticles will decrease the overall tackiness of the pressure sensitive adhesive composition. The addition of a large proportion of microparticles to the pressure sensitive adhesive composition could decrease the initial adhesion of the pressure sensitive adhesive composition; while the addition of fewer microparticles will increase the peel force required for removal.

Specific applications will require tailoring the proportions of microparticles in a pressure sensitive adhesive composition. Where more initial adhesion is required, fewer microparticles will be incorporated into the pressure sensitive adhesive composition. Where a larger debonding effect is desired, more microparticles will be incorporated into the composition.

As discussed herein, a benefit of the present subject matter is that the addition of tacky microparticles to the pressure sensitive adhesive will not reduce the adhesion of the pressure sensitive adhesive composition as much as the addition of non-tacky microparticles.

In a preferred embodiment in accordance with the present subject matter, the amount of microparticles added to the pressure sensitive adhesive composition is between about 1% and about 50% by weight, and more preferably 10% by weight based upon the total weight of the pressure sensitive adhesive composition.

Figure 12:
FIG. 12 is a photograph taken under magnification of a pressure sensitive adhesive matrix containing 1% silicone microgel particles by weight, prepared in accordance with the present subject matter.
Figure 13:
FIG. 13 is a photograph taken under magnification of a pressure sensitive adhesive matrix containing 10% silicone microgel particles by weight, prepared in accordance with the present subject matter.

Referring now to FIG. 12 and FIG. 13. There is shown optical micrographs of representative silicone microgels dispersed in an acrylic adhesive matrix prepared in accordance with the present subject matter. FIG. 12 is a view of an exposed surface layer of a pressure sensitive adhesive composition containing 1% silicone gel microparticles by weight. FIG. 13 is a view of an exposed surface layer of a pressure sensitive adhesive composition containing 10% silicone gel microparticles by weight. In both FIGS. 12 and 13, the silicone gel microparticles have not been exposed to a debonding agent and are not in their swollen state.

Adhesive Matrix

Pressure sensitive adhesives are adhesives that bond to a substrate with the application of pressure. Solvents, water, chemical reaction, or heat are not required to activate the adhesive. The degree of bonding strength is influenced by the amount of pressure which is used to apply the adhesive to the surface. Bonding strength is also affected by substrate characteristics such as smoothness, surface energy, presence of contaminants, and the like. Pressure sensitive adhesives are usually designed for use at room temperature. They normally display a total or partial loss of bonding strength at low temperatures and shear holding ability at high temperatures.

Pressure sensitive adhesives exhibit viscoelastic properties, which are tailored to ensure proper adhesion. Pressure sensitive adhesives are designed to balance their tendency to flow (adhesive forces) and their resistance to flow (cohesive forces). Pressure sensitive adhesives form a bond to a surface because their adhesive forces are such that they flow, or wet the substrate. The bond maintains strength because the cohesive forces of the pressure sensitive adhesive are such that they resist flow when stress is applied to the bond.

Once the substrate and the pressure sensitive adhesive are in proximity, there are also molecular interactions, such as van der Waals forces involved in the bond, which contribute significantly to the bond strength.

Pressure sensitive adhesives are usually composed of elastomeric polymers with or without tackifiers. A variety of polymers have been used to manufacture pressure sensitive adhesives; for example, acrylic and methacrylic ester homo- or copolymers, butyl rubber-based systems, silicones, nitriles, styrene block copolymers, ethylene-vinyl acetate, urethanes, vinyl esters and amides, olefin copolymer materials, natural or synthetic rubbers, and the like.

Pressure sensitive adhesives are typically classified in one of two categories, permanent and removable.

Permanent pressure sensitive adhesives are adhesives which do not allow for the removal of an adhesive article from a substrate without considerable damage to the article, adhesive failure at the article surface, cohesive failure in the body of the adhesive, or residual transfer of the adhesive to the substrate.

The adhesion of removable pressure sensitive adhesives is considerably lower, allowing removal of the article from the substrate even after a protracted period of contact. Removal is accomplished without significant damage to the article or substrate. Removable pressure sensitive adhesives form a temporary bond and can be removed without leaving any residue on the substrate. Removable pressure sensitive adhesives can be applied to surface protection films, masking tapes, bookmark and note papers, price marking labels, promotional graphics materials, and skin contacting articles, i.e., wound dressings, EKG electrodes, analgesic and transdermal drug patches, medical or athletic tape, etc.

Pressure sensitive adhesives can be prepared with either a liquid carrier or in solid form. Articles made from liquid pressure sensitive adhesives are coated with the adhesive and the solvent or water carrier is evaporated. They may be further heated to initiate a crosslinking reaction in the polymer and increase molecular weight. Solid form pressure sensitive adhesives may be low viscosity polymers that are coated and then reacted with radiation to increase molecular weight and form the adhesive; or they may be high viscosity materials that are heated to reduce viscosity enough to allow coating, and then cooled to their final form.

The specific application for the adhesive composition will determine the properties necessary for the pressure sensitive adhesive.

Adhesives may be applied directly to a substrate or by a carrier, and depending upon the utility, can be applied to a backing material or carrier layer using techniques such as spraying, wire coating, knife coating, Meyer Bar coating, curtain coating, extrusion coating, or gravure print coating.

The preferred embodiment for the adhesive matrix of the present subject matter is comprised of a pressure sensitive adhesive. The pressure sensitive adhesive is a continuous first phase of the adhesive composition that contains a discontinuous second phase of microparticles. The pressure sensitive adhesive will preferably not chemically react or dissolve the microparticles. The microparticles will readily blend into the adhesive upon mixing. The pressure sensitive adhesive is preferably not soluble in aqueous solutions or in the selective debonding agent. The matrix maintains the general uniform dispersion of microparticles in suspension over time. The particles will not settle out of or migrate to a particular region of the adhesive matrix.

The pressure sensitive adhesive is preferably comprised of a solvent acrylic adhesive. Other pressure sensitive adhesives can be used; such as an acrylic polymer, a polyurethane adhesive, a rubber adhesive, or the like. The pressure sensitive adhesive may be formed by solvent, bulk and emulsion polymerization including dispersion and suspension polymerization and formed of any combination of polymers and additives which when combined will provide a pressure sensitive adhesive product having a glass transition temperature less than about 10° C. below use temperature, typically less than about 30° C. below use temperature. As used herein, the phrase "use temperature" is the temperature at which the adhesive is normally bonded to a substrate. Use temperature is normally ambient (25°) but may be 0° C. or less for low temperature applications and higher than 25° C. for high temperature applications.

The copolymers for the adhesive of the instant subject matter can be stabilized against UV and oxidative degradation by using UV stabilizers and antioxidants. Fillers, colorants, tackifiers, plasticizers, oils, and the like, may also be added.

When applied to an adhesive article, the matrix preferably completely contains the microparticles and forms a practically smooth substrate-contacting surface. The pressure sensitive adhesive will preferably be more tacky than the microparticles and provide the majority of adhesion when used as part of an adhesive article.

The adhesive composition will be applied to an adhesive article by any practical means, such as spraying, wire coating, dip coating, knife coating, Meyer Bar coating, curtain coating, extrusion coating, or gravure print coating. The adhesive composition will remain affixed to the backing material of an adhesive article even upon exposure to the debonding agent. The adhesive composition will preferably be applied in layers having a thickness of about 30 to about 100 micrometers.

Regardless of the pressure sensitive adhesive chosen for the adhesive matrix, it is preferred that the pressure sensitive adhesive be insoluble in the selective debonding agent. To choose a pressure sensitive adhesive that could dissolve in the debonding agent would lead to undesirable consequences. When the debonding agent is applied to an article containing the pressure sensitive adhesive, the pressure sensitive adhesive could partially or totally dissolve; leaving a residue on the substrate after removal of the article. The present subject matter and related embodiments alleviate this problem by incorporating a pressure sensitive adhesive that does not chemically react with the selective debonding agent.

In a preferred embodiment, the pressure sensitive adhesive will not damage the adhesive article, will not undergo adhesive failure at the article surface, undergo cohesive failure in the body of the adhesive, or transfer residue to the substrate upon debonding in accordance with the present debonding techniques.

Selective Debonding Agents

Debonding agents assist in removing an adhesive article from a substrate. Debonding agents can include fluids, heat, pH changes, chemical reactions, or the like. At their most basic level, debonding agents are exposed to an adhesive and reduce or eliminate its adhesive properties.

Additives can be incorporated into the adhesive, such as microparticles, which provide a mechanism to assist in debonding. Where additives are incorporated, the debonding agent acts on the additive to bring about the debonding effect. In these systems, it is also possible that the debonding agent acts on the adhesive itself to assist in debonding.

The debonding agent can be "selective" in that it chemically reacts with the debonding additive such as the microparticles yet does not react with the adhesive.

The selection of the debonding agent will be determined based on the type of adhesive, the intended application, the type of additive, cost of production, cost of debonding, environmental factors, and the like.

In one embodiment of the present subject matter, the debonding agent will preferably be absorbed and react with the microparticles, causing them to expand. When incorporated into an adhesive article, the expanded microparticles decrease the bonding force at the interface between the substrate and adhesive composition and assist in debonding in accordance with the present subject matter.

In another preferred embodiment, the debonding agent will preferably be absorbed and react with the microparticles, causing them to change shape. When incorporated into an adhesive article, the shape change in the microparticles decreases the bonding force at the interface between the substrate and adhesive composition and assists in debonding in accordance with the present subject matter.

In both embodiments, it is preferred that the debonding agent be "selective" in that it will not chemically react with the adhesive and only react with the microparticles of the adhesive composition. If the debonding agent reacts with the adhesive matrix, it could leave an undesirable tacky residue on the substrate subsequent to removal.

The selective debonding agent preferably includes hexamethyldisiloxane (HMDS). Other suitable debonding agents preferably include silicone oil, a hydrocarbon oil, a mineral oil, or other small molecule silicones. The term "small molecule" refers to molecules having a molecular weight of less than about 200, more preferably less than 175, and more preferably less than 165. Additional examples of the selective debonding agent include but are not limited to silicones, perfluoroalkyl derivatives, low molecular weight oils, aqueous compositions, alkyl esters, limonene derivatives, paraffin solvents, hydrocarbon solvents, alkyl ethers, aromatic esters, surfactants, and combinations thereof. Combinations of one or more of these agents are also included in the present subject matter.

Adhesive Systems

The present subject matter also includes various adhesive systems which are selectively debondable upon exposure to, or administration of, one or more debonding agents. The adhesive systems comprise the adhesive compositions as described herein, and the debonding agent(s) as described herein.

Specifically, the present subject matter provides a selectively debondable adhesive system. The system comprises a selective debonding agent and a pressure sensitive adhesive composition. The pressure sensitive adhesive composition includes a pressure sensitive adhesive and crosslinked silicone gel microparticles dispersed therein. The microparticles are such that they undergo an increase in volume and/or a change in shape when exposed to the selective debonding agent.

Methods of Preparation

Pressure sensitive adhesive matrices containing silicone gel microparticles in accordance with the present subject matter are depicted in FIGS. 1 2, and 3. In one aspect of the present subject matter, a methods of preparing such adhesive compositions are provided. The methods comprise certain operations as described herein. The methods provide for a simple production process that easily forms and combines the silicone gel microparticles with the pressure sensitive adhesive.

Figure 7:
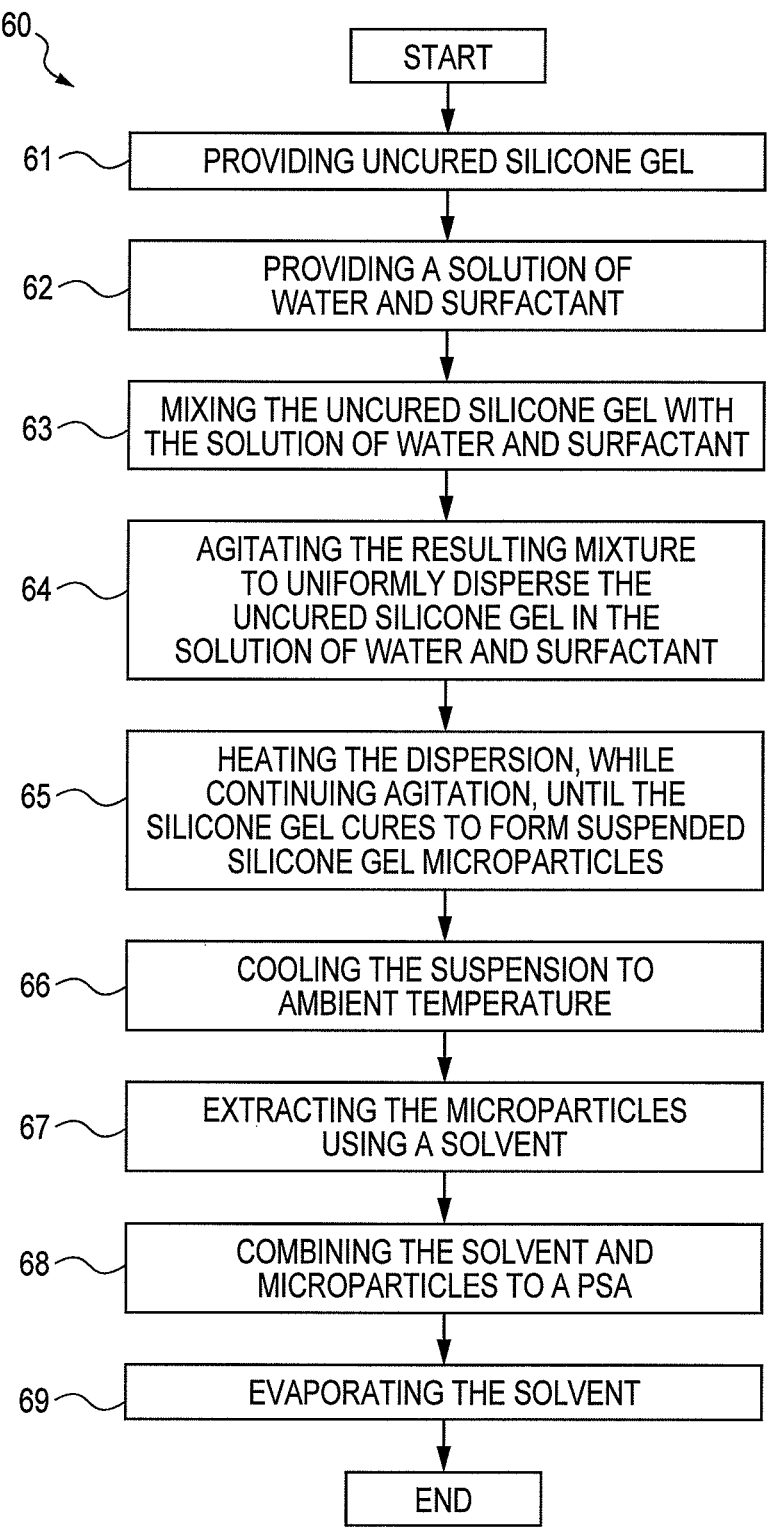
FIG. 7 is a flowchart of an exemplary method for preparing the pressure sensitive adhesive composition is accordance with the subject matter.

Referring now to FIG. 7, a preferred method 60 generally comprises the operations of: providing uncured silicone gel depicted as operation 61; providing a solution of water and surfactant, shown as operation 62; mixing the uncured silicone gel with the solution of water and surfactant, shown as operation 63; agitating the resulting mixture to uniformly disperse the uncured silicone gel in the solution of water and surfactant, depicted as operation 64; heating the dispersion, while continuing agitation, until the silicone gel cures to form suspended silicone gel microparticles in the solution, shown as operation 65; cooling the suspension to ambient temperature, shown as operation 66; extracting the microparticles using a solvent, depicted as operation 67; combining the solvent and microparticles to a pressure sensitive adhesive, noted as operation 68; and evaporating the solvent, shown as operation 69.

The operation 61 of the method 60 preferably includes utilizing a two-part (parts A and B) silicone gel component system. The component system is comprised of a reactive silicone polymer (A) and crosslinking agent (B). Both parts A and B have a similar vinyl-substituted polydimethylsiloxane bases. The reactive silicone polymer (A) contains hydrogen atoms bonded directly to the silicon atom. The crosslinking agent (B) contains at least one vinyl-substituted polydimethylsiloxane as well as a catalyst. The catalyst contains a platinum or rhodium metal complex, and more preferably organometallic compounds. The reactive silicone polymer (A) and the crosslinking agent (B) are typically combined thoroughly in a beaker or other appropriate container just prior to mixing them into the solution of water and surfactant. Part A is preferably combined in the amount of about 6.5% by weight of the entire suspension. Part B is preferably combined in the amount of about 6.7% by weight of the entire suspension. The resultant combined silicone will be uncured and in liquid form at this point.

Operation 62 of the method 60 preferably includes utilizing sodium lauryl sulfate as a surfactant in the amount of about 0.6% by weight of the entire suspension and water in the amount of about 86.2% by weight of the entire suspension. The water and surfactant are mixed thoroughly in a beaker or other appropriate container before the uncured liquid silicone is added. Other anionic sulfate surfactants in similar amounts can preferably be used such as ammonium lauryl sulfate, sodium laureth sulfate, sodium myreth sulfate, or the like.

Operation 63 of the method 60 preferably includes mixing the uncured liquid silicone from the operation 61 with the solution of water and surfactant of the operation 62. The mixing is accomplished by pouring, or other like means, the uncured liquid silicone into the water and surfactant solution which is contained in a beaker or other appropriate container.

Once combined, the agitation operation 64 of the method 60 preferably includes agitating the mixture. This preferably can include stirring, shaking, mixing, beating, folding, swirling, whipping, whisking or blending the uncured liquid silicone gel and water and surfactant solution at a rate so as to disperse the uncured liquid silicone uniformly throughout the water and surfactant solution.

Operation 65 of the method 60 preferably includes heating the dispersion of the operation 64 to a temperature within a range of about 30° C. to about 35° C. for about three hours while preferably continuing to agitate the dispersion. This can be accomplished on a hot plate with a stir bar mechanism or by other conventional heating and agitating means. Industrial mixers and heaters can be employed for large scale batch production. The heating actuates the curing of the liquid silicone into a gel. It is preferable that a complete cure is attained. Alternatively, and for other various applications, a partial cure will be desired. The time required for the desired curing amount depends on various factors, such as, for example, the reaction temperature or the catalyst concentration. The continued agitation in this step will keep the liquid silicone gel dispersed in solution during the gel curing process.

The rate of agitation will affect the size of the final product of silicone gel microparticles. Increasing the agitation will decrease the size of the silicone gel microparticles. Conversely, decreasing the agitation will increase the size of the silicone gel microparticles. Preferably, the agitation rate will be such as to produce microparticles having a span of from about 10 to about 50 micrometers at their largest cross section. Since pressure sensitive adhesives are normally layered in 30 to 100 micrometer layers, the microgel particles are more preferably between 5 and 30 micrometers in size. According to this process the microgel particles have a homogeneous, essentially monodispersed size distribution.

In heating and agitation operation 65, one can control the characteristics of the silicon gel microparticles by adjusting the extent of crosslinking. Controlling the amount of crosslinking can be done by varying the ratio of the silicone crosslinker (part B) to the reactive silicone polymer (part A). Increasing the amount of silicone crosslinker will increase the crosslink density. This will result in less swelling of the microgel particles, a harder gel, and microgel particles that will dissolve less in the selective debonding agent.

The cooling operation 66 of the method 60 includes removing the suspension from the heat and agitation source after the silicone gel has cured. The suspension is allowed or induced to cool to ambient temperature. In another aspect, this operation is removed and the suspension is kept at an elevated temperature above ambient. This will aid in the evaporation of the solvent in subsequent operation(s) of the method 60.

The extraction operation 67 of the method 60 preferably includes using toluene as the solvent in the extraction step. In other preferred embodiments, other water-insoluble organic solvents can be used. Ordinary extraction procedures are employed and include adding an amount of liquid solvent to the suspension. The suspension is then agitated to an extent to evenly distribute the solvent throughout the suspension. The agitation is then discontinued and the suspension is allowed to settle. This will result in the solvent and water essentially separating into two layers within the container. A portion of the silicone gel microparticles will migrate into the layer of solvent that has separated from the water solution. After settling, the solvent and silicone microgel particles can be removed from the container with a pipette or other suitable means. The ratio by weight of silicone gel microparticles in the solvent suspension can be controlled with the adjustment of the amount of solvent initially added. More solvent will result in a lower concentration of silicone gel microparticles. Less solvent will result in a higher concentration of silicone gel microparticles. In another aspect, where the cooling operation 66 is not performed, extraction will take place directly after the heating and agitation operation 65 in which the silicone gel cures to form microparticles.

The combining operation 68 of the method 60 preferably includes combining the solvent and silicone microgel particles with the pressure sensitive adhesive by physical mixing. In one aspect, the combining is performed in a manner that provides dispersion throughout the adhesive matrix of silicone gel microparticles. In another aspect, the combining is performed in a manner that provides microparticle dispersion confined to one surface or region of the pressure sensitive adhesive layer. Combining techniques will influence the dispersion of microparticles within the pressure sensitive adhesive composition.

Combining techniques are preferably customized in order to prepare the dispersion arrangements as depicted in FIG. 1 and FIG. 2. To attain dispersion as shown in FIG. 1, the solvent and microgels are physically mixed into a solvent acrylic pressure sensitive adhesive. The mixing can be attained by simple physical stirring or like means. The mixing will continue until the suspension and pressure sensitive adhesive are thoroughly combined. The resulting combined composition is periodically referred to herein as an intermediate product.

To attain the pressure sensitive adhesive configuration depicted in FIG. 2, a number of techniques can be used. One preferred embodiment includes applying a layer of pressure sensitive adhesive to a backing material. The solvent containing the microgels is then poured onto the exposed pressure sensitive adhesive. The solvent will partially dissolve the exposed face of the pressure sensitive adhesive and also begin to evaporate. During this process, the microgels will migrate into the exposed face of the pressure sensitive adhesive. When a majority of the solvent is evaporated, the microgels will be contained within just the exposed face of the pressure sensitive adhesive and not throughout the layer of pressure sensitive adhesive.

Another technique to attain the pressure sensitive adhesive configuration depicted in FIG. 2 includes pouring the solvent and suspended microgels into a container so as to form a thin layer of liquid. A pressure sensitive adhesive is then applied over the solvent microgel liquid layer. The solvent and microgels will migrate into the pressure sensitive adhesive layer covering them. The solvent will then evaporate leaving the microgels in the face initially exposed to the solvent suspension.

A third process to attain the pressure sensitive adhesive configuration depicted in FIG. 2 involves combining the solvent and microgels to a pressure sensitive adhesive and mixing to distribute the microgel in the pressure sensitive adhesive. The excess solvent is then evaporated from the pressure sensitive adhesive matrix. A thin layer, approximately 10 to 30 microns in thickness, of this pressure sensitive adhesive matrix is applied over a thick layer, approximately 20 to 70 microns in thickness, of pressure sensitive adhesive that does not contain the microgels. The two layers of pressure sensitive adhesive form one cohesive layer with microgels at one surface of the pressure sensitive adhesive as depicted in FIG. 2.

Preferably, a solvent acrylic adhesive is used for the matrix. A solvent acrylic adhesive allows for blending into the adhesive of the solvent and silicone gel microparticles.

The evaporation operation 69 of the method 60 preferably includes evaporating at least a portion of and typically, the excess solvent from the pressure sensitive adhesive composition. The evaporation of the excess solvent allows the pressure sensitive adhesive to function properly and maintain its proper adhesive and cohesive forces. Excess solvent disturbs the balance between these two characteristics and diminish the effectiveness of the pressure sensitive adhesive.

The evaporation step can be done by providing time for the excess solvent to evaporate on its own or by speeding up the process by the application of external heat or energy.

In one aspect, the preferred method 60 can produce silicone gel microparticles that are dispersed within the pressure sensitive adhesive at an amount between 1 to 50% by weight. The amount of time required to dissolve the excess solvent is dependent on the amount of solvent used in the extraction operation 67, the temperature, and agitation rate. Agitation during evaporation (operation 69) can continue and would aid in the evaporation of excess solvent. In another aspect, and to attain dispersion according to FIG. 2, agitation of the pressure sensitive adhesive matrix would not be incorporated.

Increasing the temperature of the pressure sensitive adhesive matrix would also aid in solvent evaporation. This could be done by utilizing an external heat source or by skipping the cooling operation 66 of the method 60 and maintaining the elevated temperature of the pressure sensitive adhesive matrix during all subsequent operations 67, 68 and 69.

It will be understood that the aforementioned steps for preparing a tacky silicone gel are provided for exemplary purposes and the subject matter is not meant to be limited by such steps or operations. Any suitable steps for preparing silicone gel microparticles dispersed in a pressure sensitive adhesive may be used while still being within the scope of the present subject matter. Thus, the present subject matter includes variations of method 60 in which one or more of operations 61-69 are not utilized. The subject matter also includes variations of method 60 including one or more additional operations.

The silicone gel microparticles formed from the method 60 are preferably soft, clear, tacky silicone gel microparticles that are at least partially crosslinked with medium crosslink density. The silicone gel microparticles preferably swell to about 3 to about 20 times their original size upon exposure to volatile small molecule silicone fluids such as hexamethyldisiloxane (HDMS) and do not swell upon exposure to aqueous fluids. The silicone gel microparticles preferably do not react with the pressure sensitive adhesive matrix. The silicone gel microparticles do not swell or change shape as a result of being exposed to the pressure sensitive adhesive. The silicone gel microparticles preferably do not react with aqueous solutions. The silicone gel microparticles do not swell or change shape as a result of being exposed to aqueous solutions.

The tacky silicone gel is produced by thoroughly mixing parts A and B in a ratio of about 1:1. The properties of the fully cured silicone can be influenced in various different ways—e.g. through varying the ratio of the components A and B, by modifying the stoichiometric ratios of the groups responsible for the crosslinking—such as the vinyl groups and silicon-hydrogen groups, through the molecular weights of the polysiloxanes used or through the concentration of the filling agent(s) used. In this way silicon gels can be made available that are soft, very adhesive and not friable and exhibit significant adhesion to the skin.

Articles

Figure 4:
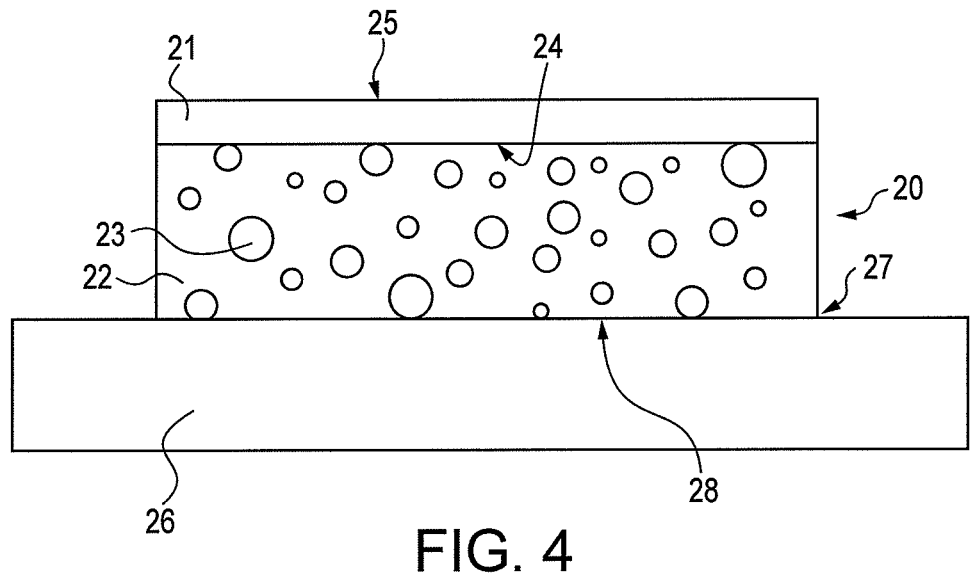
FIG. 4 is a schematic, cross sectional view of a preferred embodiment adhesive article adhered to a substrate in accordance with the present subject matter.

Another embodiment of the present subject matter includes articles utilizing the pressure sensitive adhesive composition. Referring now to FIGS. 4, 5, 9, 10 and 11, shown are preferred embodiment articles of the present subject matter. In particular, FIG. 4 depicts a sectional view of a preferred embodiment adhesive article 20 adhered to a substrate 26 in accordance with the present subject matter. The article 20 comprises a backing layer 21 with a first side 24 and a second oppositely directed side 25. A pressure sensitive adhesive matrix 22 containing dispersed microparticles 23 is disposed or positioned on the first side 24 of the backing layer 21. An exposed adhesive face 28 of the article 20 is applied to the substrate 26 forming an article-substrate interface 27.

Figure 5:
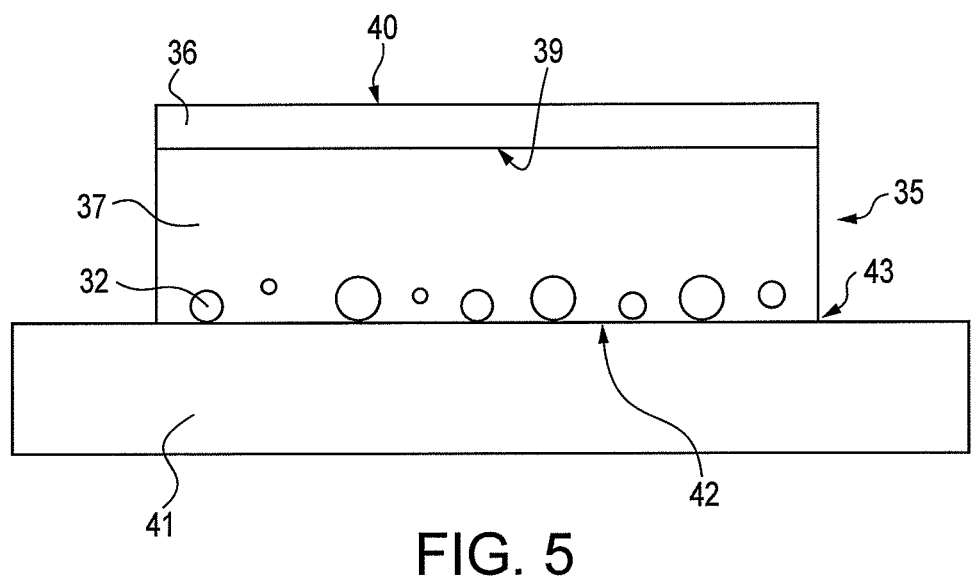
FIG. 5 is a schematic, cross sectional view of another preferred embodiment adhesive article adhered to a substrate in accordance with the present subject matter.

FIG. 5 depicts a sectional view of a preferred embodiment adhesive article 35 adhered to a substrate 41 in accordance with the present subject matter. The article 35 comprises a backing layer 36 with a first side 39 and a second oppositely directed side 40. A pressure sensitive adhesive matrix 37 containing microparticles 32 dispersed along or proximate to an exposed adhesive face 42 is disposed on the first side 39 of the backing layer 36. An exposed adhesive face 42 of the article 35 is applied to the substrate 41 forming an article-substrate interface 43.

Figure 9:
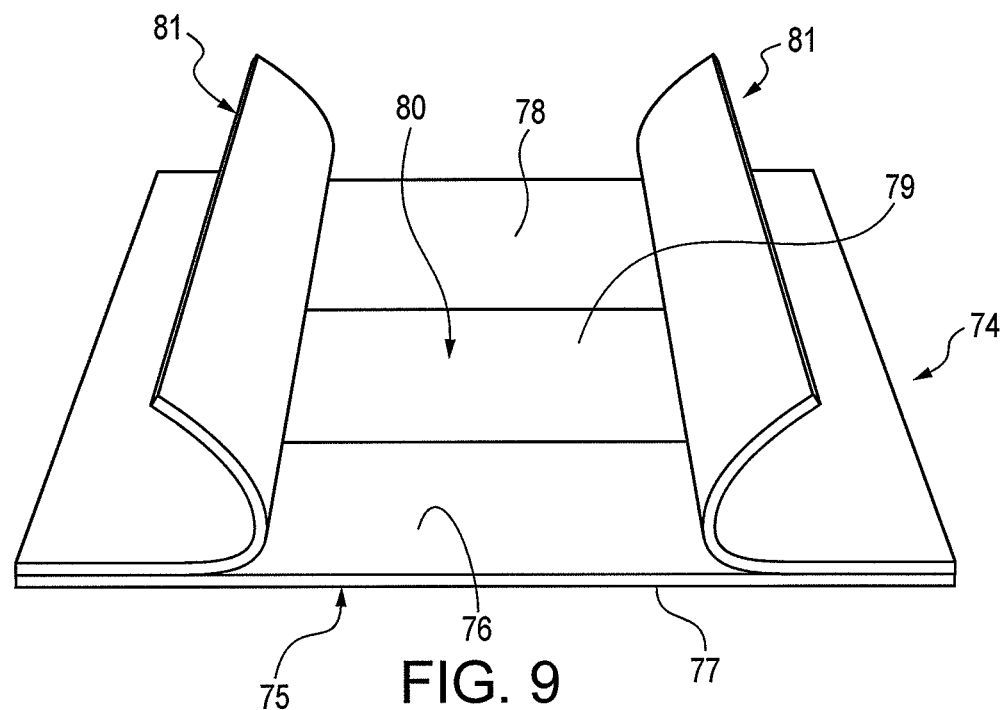
FIG. 9 is a schematic view of a preferred embodiment adhesive article with a release liner partially removed in accordance with the subject matter.

FIG. 9 depicts a polygonal multi-layer wound dressing 74. The dressing comprises a backing layer 75 that has a first surface 76 and an oppositely directed second surface 77. A pressure sensitive adhesive composition 78 of the present subject matter is disposed along the first surface 76 of the backing layer 75. A dressing 79, such as gauze, is also located on the first surface 76 of the backing layer 75. This comprises the wound contacting side 80 of the wound dressing 74. A product release liner 81 is optionally included. The release liner 81 preferably covers the adhesive composition 78.

Figure 10:
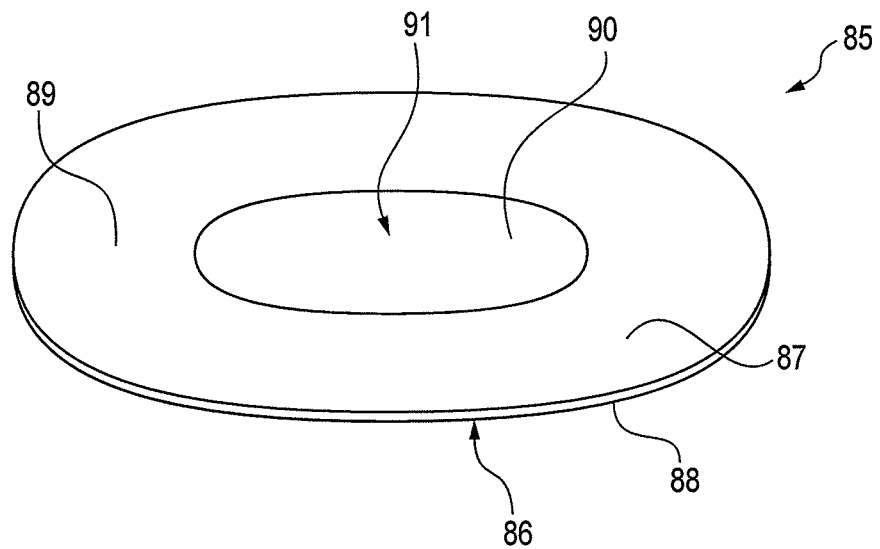
FIG. 10 is a schematic view of another preferred embodiment adhesive article without a release liner in accordance with the subject matter.

FIG. 10 depicts an elliptical wound dressing in accordance with another preferred embodiment of the present subject matter. The elliptical wound dressing 85 comprises a backing layer 86 that has a first surface 87 and a second oppositely directed surface 88. A pressure sensitive adhesive composition 89 of the present subject matter is disposed or positioned along the first surface 87 of the backing layer 86. A dressing 90, such as gauze, is also located centrally on the first surface 87 of the backing layer 86. This comprises the wound contacting side 91 of the wound dressing 85. Although the wound dressing 85 in FIG. 10 is depicted with no product release liner, it will be appreciated that such liner could be included in accordance with the present subject matter and the figure in no way limits the embodiment.

Figure 11:
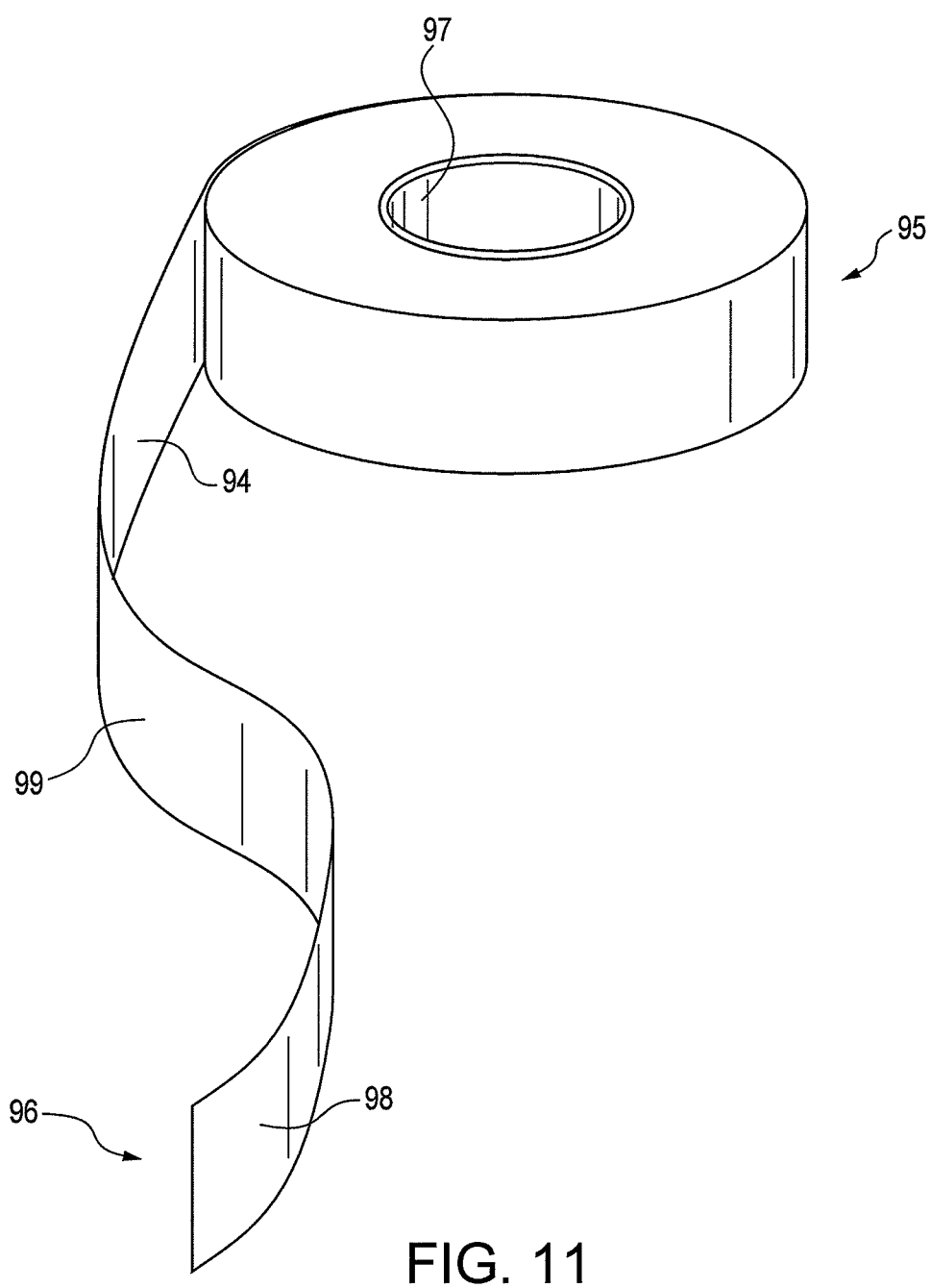
FIG. 11 is a perspective view of a preferred embodiment adhesive tape in accordance with the present subject matter.

FIG. 11 depicts a roll of tape in accordance with another preferred embodiment of the present subject matter. The tape 95 comprises an elongated backing layer 96 rolled around a central cylindrical core 97. The backing layer 96 defines a first surface 98 and second oppositely directed surface 99. A pressure sensitive adhesive composition 94 of the present subject matter is disposed on the first surface 98 of the backing layer 96 and optionally on the second surface 99 (not depicted). The second surface 99 of the backing layer can optionally have a product release coating or layer, such as Teflon or other silicon base, applied to it so as to allow the pressure sensitive adhesive composition 94 to easily release from it. The tape 95 could optionally include a product release liner (not depicted) adhered over the pressure sensitive adhesive composition 94 along its entire length or portions thereof.

The backing layer of the preferred embodiments is preferably comprised of a thin polymeric elastic or flexible film coating providing a bacterial barrier formed from a water vapor permeable pliable elastomer material. The film is continuous in that it has no perforations or pores which extend through the thickness of the film. Films of this type are known and generally are hydrophilic polymeric materials through which water may diffuse. The backing layer is preferably selected from the group consisting of polyurethane, microporous films of polyolefin, polyester, poly (caprolactam), poly (N-vinylidene fluoride), nylon, cellulous acetate. Combinations of these materials can also be used. Other layers or material can optionally be incorporated into the articles of the present subject matter, including a carrier layer.

Suitable continuous conformable backing layers have a moisture vapor transmission rate (MVTR) of the backing layer alone of about 1,500 to about 14,600 $g/m^2/24$ hrs, preferably 2500 to 2700 $g/m^2/24$ hrs at 38° C. The backing layer thickness is preferably in the range of about 15 to about 45 micrometers, more preferably 30 micrometers.

In certain embodiments, the pressure sensitive adhesive matrix is disposed on the backing layer at a thickness of from about 30 to about 100 micrometers.

Another preferred embodiment article incorporating the pressure sensitive adhesive composition of the present subject matter is a glue. The glue is enclosed in a container that has a sealing mechanism. The sealing mechanism alternates between an open and closed position. When opened, the pressure sensitive adhesive composition is accessible to a user. In one embodiment the closure mechanism includes a dispensing means. In another embodiment the container is a squeezable container with a dispensing top that and has means for the glue to exit the container. In another embodiment, the glue is contained in a rigid container and the sealing mechanism includes a top with incorporated brush means to apply the pressure sensitive adhesive composition to a substrate.

The microgel particles contained within the preferred embodiment pressure sensitive adhesive compositions are between 5 and 30 micrometers in diameter. Depending on the application, the crosslink density and size of the silicone gel microparticles can be adjusted for the intended use. After being exposed to the selective debonding agent, the expanded size of the silicone gel microparticles should be between 5 and 20 times their original size, and preferably greater than 20 times their original size. The amount of silicone gel microparticles dispersed in the pressure sensitive adhesive should be between 1% and 50% by weight.

When incorporated into an article, the microgel particles are preferably uniformly dispersed within the pressure sensitive adhesive composition or alternatively preferably situated primarily at the exposed surface of the pressure sensitive adhesive composition.

The pressure sensitive adhesive is preferably a solvent acrylic adhesive and alternatively a polyurethane adhesive, a rubber adhesive, etc. Combinations of one or more of these adhesives are also included in the present subject matter. It is preferred that the adhesive not debond or dissolve when exposed to water or exudate. Combinations of one or more pressure sensitive adhesives are also included in the present subject matter.

Other articles incorporating the pressure sensitive adhesive composition of the present subject matter include a surface protective film or sheet, an ostomy adhesive article, a temporary fixing film or sheet, a fixing film or sheet, a package closure, a carrier tape, a seal tape or sheet, a label, a medical dressing, a bandage, a drape, or mechanical assembly.

Methods of Using

Pressure sensitive adhesive matrices containing silicone gel microparticles in accordance with the present subject matter are depicted in FIGS. 1 2, and 3. Articles incorporating the pressure sensitive adhesive compositions containing silicone gel microparticles in accordance with the present subject matter are depicted in FIGS. 4, 5, 9, 10 and 11. In one aspect of the present subject matter, a method of using such adhesive compositions and articles is provided.

Figure 8:
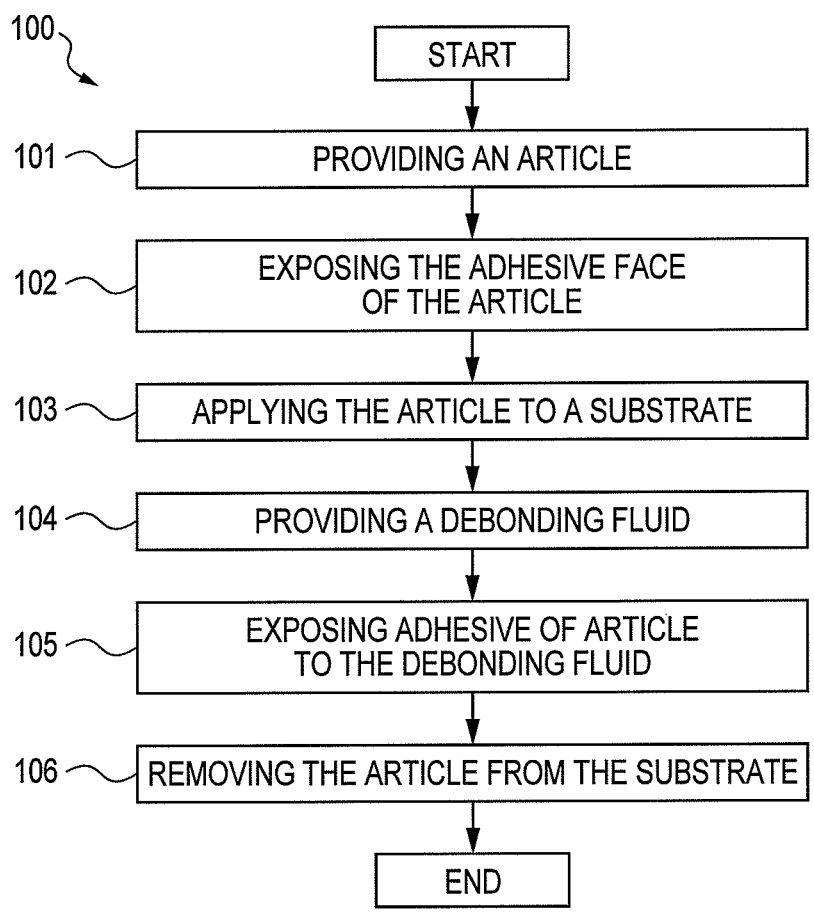
FIG. 8 is a flowchart of an exemplary method for using an adhesive article and selective debonding agent in accordance with the subject matter.

Referring now to FIG. 8, a preferred method 100 is shown comprising: providing an article, shown as operation 101; exposing the adhesive face, shown as operation 102; applying the article to a substrate, depicted as operation 103; providing a debonding fluid, shown as operation 104; exposing adhesive of article to the debonding fluid, depicted as operation 105; and removing the article from the substrate, shown as operation 106.

In operation 101, the article is any adhesive type article, such as a wound dressing or tape; or alternatively the article is the pressure sensitive adhesive composition alone. In other aspects the article is any of surface protection films, masking tapes, bookmark and note papers, price marking labels, promotional graphics materials, and skin contacting articles (i.e., wound dressings, ostomy adhesive articles, EKG electrodes, analgesic and transdermal drug patches, medical or athletic tape, etc.). In a preferred embodiment, and as discussed in the subsequent operations, the article comprises a wound dressing with solvent acrylic pressure sensitive adhesive containing silicon gel microparticles dispersed therein. It will be recognized that these operations can be incorporated to apply to any article containing a pressure sensitive adhesive composition in accordance with the present subject matter without diverting from the teaching provided herein.

In the exposing operation 102, the article preferably has a product release liner. The liner is removed to expose the wound contacting side of the wound dressing. This exposes the pressure sensitive adhesive composition and allows for adhesion of the article to a substrate of human skin. The release liners are films that easily detach from the exposed adhesive of the article. The product release liners protect the adhesive from contacting a substrate, dirt, or aqueous solutions before that intended by the user. Inadvertent contact to environmental elements can decrease the tackiness of adhesives and prevent the desired adhesion. The product release liner maintains the adhesive tackiness. Premature exposure of the wound contacting side of the article can also introduce bacteria and other contaminants into the wound area.

In the applying operation 103, the wound dressing is applied to a substrate of human skin. The application is performed by pressing the exposed surface of the pressure sensitive adhesive composition against the skin. For other article types this step is performed in a similar manner. To apply a pressure sensitive adhesive composition that is not associated with a layered article to a substrate, this operation is preferably performed by spraying, spreading, painting, or the like. The substrate can include human skin, plastic, paper, wood, masonry, metal, stone, etc. Combinations of one or more of these operations are also contemplated.

The operation 104 includes providing a debonding fluid. In this step, the debonding fluid is preferably "selective" in that it will be absorbed by the crosslinked silicone gel microparticles causing them to change shape or size from their original shape and size and at the same time, not dissolve the pressure sensitive adhesive. In a preferred embodiment, the debonding agent preferably comprises hexamethyldisiloxane (HMDS), but can alternatively be comprised of silicone oil, a hydrocarbon oil, or a mineral oil. HDMS will not dissolve the solvent acrylic pressure sensitive adhesive. HDMS will be absorbed by the silicone gel microparticles and cause them to expand.

The exposing operation 105 of the method 100 includes exposing the pressure sensitive adhesive composition of the wound dressing to the selective HDMS. The debonding agent is applied to the interface between the pressure sensitive adhesive composition and the substrate. The method of applying preferably includes using a dropper at the peel interface, relying on capillary action, spraying, painting, foaming, rubbing, soaking, submerging, brushing, pouring, vapor depositing, syringing, dabbing, squirting, immersing, and misting. This operation is also depicted graphically in FIG. 6B discussed previously.

This exposing operation 105 includes allowing the debonding agent to change the shape or size of the silicone gel microparticles within the solvent acrylic adhesive so as to decrease the bonding force of the pressure sensitive adhesive composition. The HDMS will come into contact with the silicone gel microparticles at the matrix-substrate interface. The silicone gel microparticles will absorb the HDMS and expand to from about 3 to about 20 times their original size and preferably 20 or more times their original size. Exposing the adhesive of the wound dressing to the debonding fluid can continue during the next removal step. This step is also depicted graphically in FIG. 6B discussed previously.

The removing operation 106 of the method 100 includes removing the wound dressing from the skin. Removal of the wound dressing from the skin is assisted by the silicone microgels undergoing a change in shape or size. The crosslinked gel particles will expand to about 3 to about 20 times their original size and preferably 20 or more times their original size. This increase in size reduces the and at the same time reduces the adhesion properties of the silicone microgel particles. In other embodiments, the debonding agent chosen will preferably correspond to the gel that is selected for the pressure sensitive adhesive composition. It is preferred to select a debonding agent that will not dissolve the pressure sensitive adhesive itself but only expand the microgel particles contained within. This will allow for debonding of the article without leaving any adhesive residue on the substrate. This operation is also depicted graphically in FIG. 6C discussed previously.

The present subject matter includes variations of method 100 in which one or more of operations 101-106 are not utilized. The subject matter also includes variations of method 100 including one or more additional operations.

When exposed to the selective debonding agent, the microparticles will change shape and/or size. The microgel particles will absorb a portion of the debonding agent. This can expand the particles in generally a uniform manner. One exception to that is when a microgel particle is only partially contained within the adhesive composition. The portion of the microgel that is free from the adhesive matrix and exposed to the debonding agent will deform in a different manner than the portion of the microgel particle that is still contained within the matrix. This will result in a "ballooning" effect on the portion of the microgel particle that is free of the adhesive matrix. This allows for a change, not only in size, but in shape as well. This change in shape could result in a mushroom-shaped particle.

Once the silicone microgels swell or change shape, and the adhesion of the solvent acrylic pressure sensitive adhesive is reduced, the wound dressing can be more easily removed from the skin. The force required for removal, being reduced by the swollen microgels, will produce less wound and skin irritation than ordinary wound dressing removal. In other embodiments, such as paper-to-paper interfaces, the reduction in peel force required for removal will allow for the backing layer and/or substrate to remain totally intact.

Kits

Another aspect of the present subject matter includes a kit. The preferred embodiment kits comprise an adhesive article and a selective debonding agent. In a preferred embodiment, the kit includes an adhesive article that utilizes a pressure sensitive adhesive matrix with silicone gel microparticles and a selective debonding agent comprising HDMS. The type of microgel could be altered and the debonding agent should preferably then be selected to correspond to the type of microgel particle chosen. The debonding fluid is preferably contained within a container with dropper component cap, a spray container, a container with brush component cap, a vapor-depositing mechanism, a syringe, a squirter, or equivalent.

Figure 14:
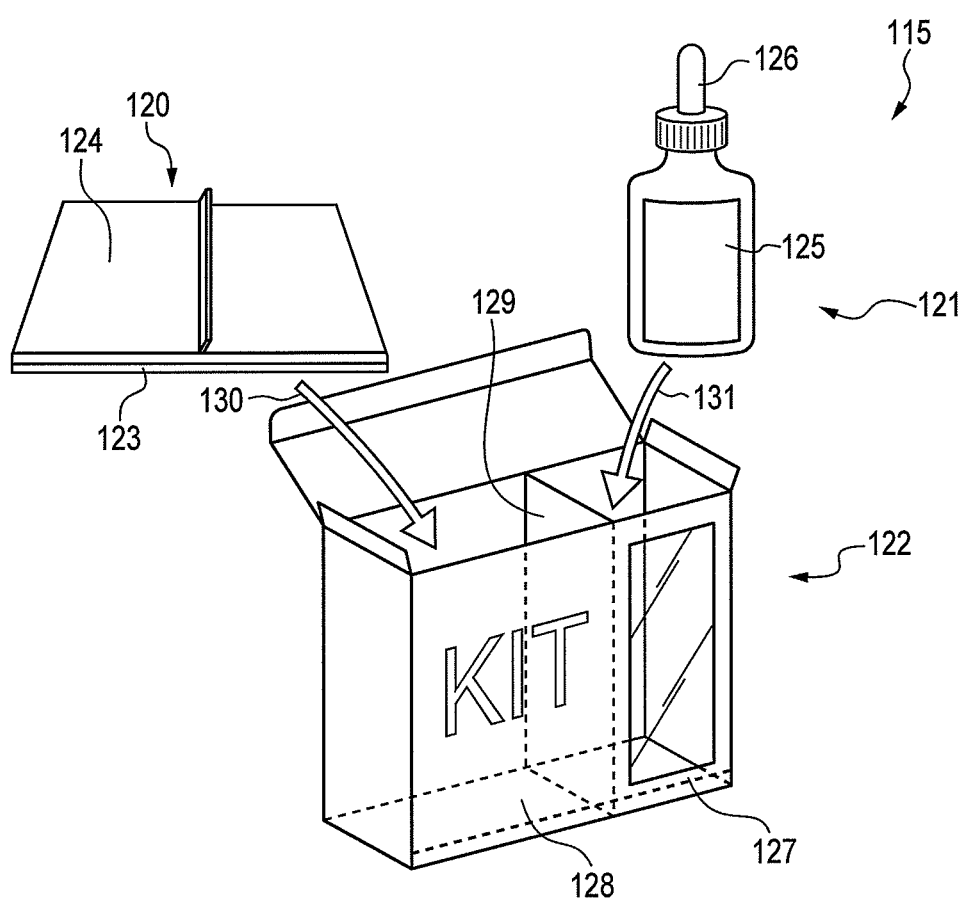
FIG. 14 is a schematic view of a preferred embodiment kit comprising an adhesive article with a release liner, a selective debonding agent, a container for the selective debonding agent, and a package in accordance with the subject matter.

Referring now to FIG. 14, shown is a preferred embodiment kit 115 of the present subject matter. In particular, FIG. 14 depicts a polygonal multi-layer adhesive article 120, a selective debonding agent 121 contained within a bottle 125 with dropper component cap 126, and a package 122 to hold these and optionally other contents of the kit.

The adhesive article 120 is shown to comprise a backing layer 123 with the pressure sensitive adhesive composition of the present subject matter disposed on a first surface and a product release liner 124 positioned over the exposed surface of the pressure sensitive adhesive composition. The wound dressing 120 optionally includes an outer individual wrapper (not shown) enclosing the individual wound dressing and identifying its contents. The kit 115 preferably includes more than one wound dressings or other types of adhesive articles. Other preferred embodiments of the adhesive article, such as tape or surgical draping, can be utilized in the kit 115.

The selective debonding agent 121 is shown to be contained within a bottle 125. The bottle is shown to have a cap 126 with integrated dropper component. The dropper is used to apply the selective debonding agent 121 to the adhesive-substrate interface. The dropper cap 126 gives the user control over the amount and location of the application means. The bottle optionally has a label identifying its contents. Other preferred embodiment containers for the selective debonding agent can be utilized in the kit.

The package 122 is shown to be a box with a compartment 127 for the selective debonding agent 121 and bottle 125, and a separate compartment 128 for the wound dressings 120. Both compartments are divided by an interior wall 129 that vertically divides the package 122. The package 122 has four sides, a bottom, and a top capable of alternating between a closed and open position. The box is depicted to have an open window for viewing of the selective debonding fluid. The package can alternatively and alternately be configured without an interior dividing wall 129 or comprise other usual forms.

The kit is assembled by placing the adhesive article 120 into its corresponding compartment 128 as depicted by arrow 130. The selective debonding agent 121 and bottle 125 are placed into corresponding compartment 127 as depicted by arrow 131. The top of the package is then closed to form the completed kit.

Within all the above mentioned embodiments of the present subject matter, one will realize that the microgel particles have their own tackiness separate and apart from the tackiness of the pressure sensitive adhesive. Upon exposure to the debonding agent and the expansion of the microgel particles, the particles lose tackiness and provide a separate and distinct mechanism for decreasing the bonding strength of the pressure sensitive adhesive matrix. This feature is preferred in that the microgel particles themselves do not significantly detract initially from the tackiness or bonding strength of the pressure sensitive adhesive in which they are contained. Again, by varying the amount of cross-linking in the silicone gel microparticles, the tackiness of the particles themselves can be adjusted for each particular application. It is known in the instant embodiments that after application of the debonding agent, there is almost an instantaneous expansion in the size of the silicone gel microparticles.

EXAMPLES

Preferred embodiment compositions comprising silicone microgels dispersed in an acrylic adhesive matrix were prepared. Silicone microgels were synthesized by curing a two-part tacky silicone gel in suspension with water. Equal parts of NuSil MED-6345 silicone gel (Part A and B) were mixed together and then dispersed in a solution of water and sodium lauryl sulfate by vigorously agitating for several minutes (Table 1). The suspended material was then heated to approximately 35° C. and cured for three hours while vigorously stirring. The resulting silicone microgels were extracted from the water and sodium lauryl sulfate solution into toluene, yielding a suspension containing approximately 2.5% solids by weight. Microscopy revealed the microgels to have a distribution of diameters centered around an average of 20 m (standard deviation=6 m).

TABLE 1

Representative Formulation to Synthesize Silicone Microgels by Suspension Curing

| Material | Amount [g] | Amount [wt-%] |
| --- | --- | --- |
| NuSil MED-6345 Part A | 0.62 | 6.5 |
| NuSil MED-6345 Part B | 0.63 | 6.7 |
| Sodium Lauryl Sulfate | 0.06 | 0.6 |
| Water | 8.16 | 86.2 |

The resulting suspension of silicone microgels in toluene was blended with wet acrylic adhesive (Avery Dennison AS-967) to create the hybrid material. Coatings approximately 80 μm thick were deposited on glass slides and imaged in a microscope to verify that silicone microgels were included and uniformly dispersed as shown in FIGS. 12 and 13.

Three different mixtures were prepared, each having a different amount of silicone. Each mixture was coated onto a siliconized PET release liner and dried at elevated temperature before laminating to a 1 mil, corona-treated polyurethane film. Strips of the laminate were cut, the release liner removed, and then adhered to the surface of a synthetic, non-biological material mimicking skin (Vitro-Skin N-19, IMS, Inc., Portland, Me.). After approximately 16 hours of dwell at room temperature, the specimens were peeled off at a rate of 100 mm/min, maintaining a peel angle of 90°. Approximately halfway through the removal process, hexamethyldisiloxane (HMDS) was added to the peel front, and continually added for the remainder of the peel. The peel force was continuously measured throughout the removal process, and an average was calculated in two regions: once before the addition of HMDS and once after.

The pre-HMDS peel force decreased monotonically with increased microgel loading. The addition of HMDS caused an abrupt 30-40% decrease in peel force in every case. Although the percentage reduction in peel force did not change dramatically with the addition of microgels, the post-HMDS peel force was lowest with the highest microgel loading.

Many other benefits will no doubt become apparent from future application and development of this technology.

All patents, published applications, and articles noted herein are hereby incorporated by reference in their entirety.

It will be appreciated that various features and functions of the above-disclosed and other subject matter, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A pressure sensitive adhesive composition adapted for selective debonding, the pressure sensitive adhesive composition comprising:
    a continuous first phase comprising a pressure sensitive adhesive matrix; and
    a discontinuous second phase comprising crosslinked silicone gel particles dispersed in the pressure sensitive adhesive matrix with a characteristic such that upon exposure to a liquid debonding agent, the particles undergo a change in at least one of shape and volume;
    wherein the silicone gel particles do not swell or change shape as a result of being exposed to aqueous solutions,
    wherein the pressure sensitive adhesive matrix includes an acrylic polymer insoluble in the debonding agent.

2. The pressure sensitive adhesive composition of claim 1 wherein prior to exposure to the debonding agent, the size of the crosslinked silicone gel particles is between 1 and 50 μm at their largest cross section.

3. The pressure sensitive adhesive composition of claim 2 wherein prior to exposure to the debonding agent, the size of the crosslinked silicone gel particles is between 5 and 30 μm at their largest cross section.

4. The pressure sensitive adhesive composition of claim 1 wherein the crosslinked silicone gel particles are at least 1% crosslinked.

5. A pressure sensitive adhesive composition adapted for selective debonding, the pressure sensitive adhesive composition comprising:
    a continuous first phase comprising a pressure sensitive adhesive matrix; and
    a discontinuous second phase comprising crosslinked silicone gel particles dispersed in the pressure sensitive adhesive matrix with a characteristic such that upon exposure to a liquid debonding agent, the particles undergo a change in at least one of shape and volume,
    wherein the crosslinked silicone gel particles are at least 50% crosslinked.

6. The pressure sensitive composition of claim 5 wherein the crosslinked silicone gel particles are at least 90% crosslinked.

7. A pressure sensitive adhesive composition adapted for selective debonding, the pressure sensitive adhesive composition comprising:
    a continuous first phase comprising a pressure sensitive adhesive matrix; and
    a discontinuous second phase comprising crosslinked silicone gel particles dispersed in the pressure sensitive adhesive matrix with a characteristic such that upon exposure to a liquid debonding agent, the particles undergo a change in at least one of shape and volume,
    wherein after exposure to the debonding agent, the size of the crosslinked silicone gel particles is between 3 and 20 times the size of the particles prior to exposure to the debonding agent.

8. The pressure sensitive adhesive composition of claim 7 wherein after exposure to the debonding agent, the size of the crosslinked silicone gel particles is between 5 and 10 times the size of the particles prior to exposure to the debonding agent.

9. A pressure sensitive adhesive composition adapted for selective debonding, the pressure sensitive adhesive composition comprising:
    a continuous first phase comprising a pressure sensitive adhesive matrix; and
    a discontinuous second phase comprising crosslinked silicone gel particles dispersed in the pressure sensitive adhesive matrix with a characteristic such that upon exposure to a liquid debonding agent, the particles undergo a change in at least one of shape and volume,
    wherein the proportion of the crosslinked silicone gel particles dispersed in the pressure sensitive adhesive matrix is at least 1% by weight;
    wherein after exposure to the debonding agent, the size of the crosslinked silicone gel particles is between 3 and 20 times the size of the particles prior to exposure to the debonding agent.

10. A pressure sensitive adhesive composition adapted for selective debonding, the pressure sensitive adhesive composition comprising:
    a continuous first phase comprising a pressure sensitive adhesive matrix; and
    a discontinuous second phase comprising crosslinked silicone gel particles dispersed in the pressure sensitive adhesive matrix with a characteristic such that upon exposure to a liquid debonding agent, the particles undergo a change in at least one of shape and volume,
    wherein the proportion of the crosslinked silicone gel particles dispersed in the pressure sensitive adhesive matrix is at least 10% by weight.

11. The pressure sensitive adhesive composition of claim 10 wherein the proportion of the crosslinked silicone gel particles dispersed in the pressure sensitive adhesive matrix is at least 20% by weight.

12. The pressure sensitive adhesive composition of claim 11 wherein the proportion of the crosslinked silicone gel particles dispersed in the pressure sensitive adhesive matrix is at least 30% by weight.

13. The pressure sensitive adhesive composition of claim 12 wherein the proportion of the crosslinked silicone gel particles dispersed in the pressure sensitive adhesive matrix is at least 40% by weight.

14. The pressure sensitive adhesive composition of claim 13 wherein the proportion of the crosslinked silicone gel particles dispersed in the pressure sensitive adhesive matrix is at least 50% by weight.

15. A pressure sensitive adhesive composition adapted for selective debonding, the pressure sensitive adhesive composition comprising:
    a continuous first phase comprising a pressure sensitive adhesive matrix; and
    a discontinuous second phase comprising crosslinked silicone gel particles dispersed in the pressure sensitive adhesive matrix with a characteristic such that upon exposure to a liquid debonding agent, the particles undergo a change in at least one of shape and volume,
    wherein the pressure sensitive adhesive matrix includes an acrylic polymer insoluble in the debonding agent.

16. A selectively debondable adhesive system comprising:
    a pressure sensitive adhesive composition including (i) a continuous first phase having a pressure sensitive adhesive matrix, and (ii) a discontinuous second phase having crosslinked silicone gel particles dispersed in the pressure sensitive adhesive matrix with a characteristic such that upon exposure to a debonding agent, the particles undergo a change in at least one of shape and volume; and
    a liquid debonding agent.

17. The adhesive system of claim 16 wherein the debonding agent includes hexamethyldisiloxane.

18. The adhesive system of claim 16 wherein the debonding agent is selected from the group consisting of silicone oil, hydrocarbon oil, mineral oil, and combinations thereof.

19. A method of debonding an article containing a selectively debondable pressure sensitive adhesive composition, the method comprising:
    providing an article containing a selectively debondable pressure sensitive adhesive composition including a continuous first phase having a pressure sensitive matrix and a discontinuous second phase having crosslinked silicone gel particles dispersed in the first phase, in which the article is adhesively bonded to a substrate so the adhesive composition and the substrate contact one another;
    providing a liquid debonding agent that induces the crosslinked silicone gel particles to undergo at least one of a change in shape from their original shape and an increase in volume, and wherein the debonding agent will not be absorbed by or dissolve the pressure sensitive adhesive;
    administering an effective amount of the liquid debonding agent to the pressure sensitive adhesive composition, whereby the crosslinked silicone gel particles with in the pressure sensitive adhesive composition undergo at least one of a change in shape and an increase in volume and thereby reduce the adhesion between the pressure sensitive adhesive composition and the substrate; and
    removing the article containing the pressure sensitive adhesive composition from the substrate.

20. The method according to claim 19 wherein the substrate is human skin.

21. The method of according to claim 19, wherein administering the debonding fluid includes at least one operation selected from the group consisting of spraying, painting, foaming, rubbing, soaking, submerging, brushing, pouring, vapor depositing, syringing, dabbing, squirting, immersing, misting, and combinations thereof.

22. A selectively debondable article, the article comprising (i) a backing material, the backing material having a first surface and an oppositely directed second surface, and (ii) a pressure sensitive adhesive composition including a continuous first phase of a pressure sensitive adhesive matrix, and a discontinuous second phase having crosslinked silicone gel particles dispersed in the first phase with a characteristic such that upon exposure to a liquid debonding agent, the particles undergo a change in at least one of shape and volume, the pressure sensitive adhesive composition disposed on at least a portion of the first surface of the backing material
    wherein the pressure sensitive adhesive matrix includes an acrylic polymer insoluble in the debonding agent.

23. The selectively debondable article according to claim 22, wherein the article further comprises a product release liner disposed on the pressure sensitive adhesive composition.

24. The article according to claim 22, wherein the backing material is selected from the group consisting of polyurethane, microporous films of polyolefin, polyester, poly(caprolactam), poly(N-vinylidene fluoride), nylon, cellulose acetate, and combinations thereof.

25. The article according to claim 22, wherein the crosslinked silicone gel particles are between 1 and 50 µm at their largest cross section.

26. The article according to claim 25 wherein the crosslinked silicone gel particles are between 5 and 30 µm at their largest cross section.

27. The article according to claim 22 wherein the crosslinked silicone gel particles are at least 1% crosslinked.

28. The article according to claim 27 wherein the crosslinked silicone gel particles are at least 50% crosslinked.

29. The article according to claim 28 wherein the crosslinked silicone gel particles are at least 90% crosslinked.

30. The article according to claim 22 wherein upon exposure to a debonding agent the crosslinked silicone gel particles undergo a change in volume of between 3 and 20 times the original size of the particles.

31. The article according to claim 22 wherein upon exposure to a debonding agent the crosslinked silicone gel particles undergo a change in volume of 20 or more times the original size of the particles.

32. The article according to claim 22 wherein the proportion of the crosslinked silicone gel particles dispersed in the pressure sensitive adhesive matrix is at least 1% by weight.

33. The article according to claim 32 wherein the proportion of the crosslinked silicone gel particles dispersed in the pressure sensitive adhesive matrix is at least 10% by weight.

34. The article according to claim 33 wherein the proportion of the crosslinked silicone gel particles dispersed in the pressure sensitive adhesive matrix is at least 20% by weight.

35. The article according to claim 34 wherein the proportion of the crosslinked silicone gel particles dispersed in the pressure sensitive adhesive matrix is at least 30% by weight.

36. The article according to claim 35 wherein the proportion of the crosslinked silicone gel particles dispersed in the pressure sensitive adhesive matrix is at least 40% by weight.

37. The article according to claim 36 wherein the proportion of the crosslinked silicone gel particles dispersed in the pressure sensitive adhesive matrix is at least 50% by weight.

38. The article according to claim 22 wherein the pressure sensitive adhesive composition comprises an acrylic polymer.

39. The article of claim 22 wherein the article is selected from the group consisting of a surface protective film or sheet, a masking film or sheet, a temporary fixing film or sheet, a non-temporary fixing film or sheet, a carrier tape, a seal tape or sheet, a label, a medical dressing, a bandage, and a drape.

40. A kit comprising:
a backing material having a first surface and an oppositely directed second surface,
a pressure sensitive adhesive composition disposed on at least a portion of the first surface of the backing material, the pressure sensitive adhesive composition adapted for selective debonding and including a pressure sensitive adhesive matrix, crosslinked silicone gel particles dispersed in the pressure sensitive adhesive matrix with a characteristic such that upon exposure to a debonding agent, the particles undergo a change in at least one of shape and size;
a selective liquid debonding agent for removing the adhesively applied backing material from the surface; and
a container retaining the selective debonding agent.

41. The kit of claim 40 further comprising:
a package to contain the backing material and the pressure sensitive adhesive disposed thereon, the container and the debonding agent.

42. The kit of claim 40 wherein the pressure sensitive adhesive composition of the backing material exhibits a tackiness that decreases after the selective debonding agent is applied.

43. The kit of claim 40 wherein the selective debonding agent is selected from the group consisting of hexamethyldisiloxane, silicones, perfluoroalkyl derivatives, low molecular weight oils, aqueous compositions, alkyl esters, limonene derivatives, paraffin solvents, hydrocarbon solvents, alkyl ethers, aromatic esters, surfactants, and combinations thereof.

44. The kit of claim 40 wherein the container includes a spray device.

45. The kit of claim 40 wherein the container includes a roll-on device.

46. The kit of claim 40 wherein the container includes a brush-on device.

47. The kit of claim 40 wherein the backing material is incorporated in a medical product selected from the group consisting of bandages, dressings, gauze, tape, wound closure covers, closure strips, and pads.

* * * * *